US011229575B2

(12) United States Patent
Capelli et al.

(10) Patent No.: US 11,229,575 B2
(45) Date of Patent: Jan. 25, 2022

(54) METHODS OF TREATING CELLULITE AND SUBCUTANEOUS ADIPOSE TISSUE

(71) Applicant: SOLITON, INC., Houston, TX (US)

(72) Inventors: Christopher C. Capelli, Houston, TX (US); David Robertson, Houston, TX (US)

(73) Assignee: SOLITON, INC., Houston, TX (US)

( * ) Notice: Subject to any disclaimer, the term of this patent is extended or adjusted under 35 U.S.C. 154(b) by 791 days.

(21) Appl. No.: 15/573,353

(22) PCT Filed: May 12, 2016

(86) PCT No.: PCT/US2016/320069
§ 371 (c)(1),
(2) Date: Nov. 10, 2017

(87) PCT Pub. No.: WO2016/183307
PCT Pub. Date: Nov. 17, 2016

(65) Prior Publication Data
US 2018/0116905 A1 May 3, 2018

Related U.S. Application Data

(60) Provisional application No. 62/160,147, filed on May 12, 2015, provisional application No. 62/277,796, filed on Jan. 12, 2016.

(51) Int. Cl.
*A61N 7/00* (2006.01)
*A61H 23/00* (2006.01)
*A61B 17/225* (2006.01)

(52) U.S. Cl.
CPC .............. *A61H 23/008* (2013.01); *A61N 7/00* (2013.01); *A61B 17/225* (2013.01);
(Continued)

(58) Field of Classification Search
CPC .......... A61H 23/008; A61H 2201/0153; A61H 2201/1207; A61H 2201/1238;
(Continued)

(56) References Cited

U.S. PATENT DOCUMENTS 3,364,708 A   1/1968   Padberg
3,604,641 A   9/1971   Wilson et al.
(Continued)

FOREIGN PATENT DOCUMENTS

CN    101028525    9/2007
CN    101146574    3/2008
(Continued)

OTHER PUBLICATIONS

Boxman, et al., "Handbook of Vacuum Arc Science and Technology: Fundamentals and Applications," Park Ridge, New Jersey: Noyes Publications, pp. 316-319, 1995.
(Continued)

*Primary Examiner* — Peter Luong
(74) *Attorney, Agent, or Firm* — Norton Rose Fulbright US LLP

(57) ABSTRACT

Embodiments of the present disclosure are directed to methods of inducing therapeutic adipose tissue inflammation using high frequency pressure waves (e.g. high frequency shockwaves) wherein the inflammation results in a reduction in the volume of subcutaneous adipose tissue. Embodiments include applying electrohydraulic generated shockwaves at a rate of between 10 Hz and 100 Hz to reduce the appearance of cellulite or the volume of subcutaneous fat in a treatment area.

25 Claims, 16 Drawing Sheets

(52) U.S. Cl.
CPC ........... *A61H 2201/0153* (2013.01); *A61H 2201/1207* (2013.01); *A61H 2201/1238* (2013.01); *A61H 2205/06* (2013.01); *A61H 2205/083* (2013.01); *A61H 2205/086* (2013.01); *A61H 2205/108* (2013.01); *A61H 2207/00* (2013.01); *A61N 2007/0008* (2013.01); *A61N 2007/0034* (2013.01); *A61N 2007/0065* (2013.01)

(58) Field of Classification Search
CPC .......... A61H 2205/06; A61H 2205/083; A61H 2205/086; A61H 2205/108; A61H 2207/00; A61N 7/00; A61N 2007/0008; A61N 2007/0034; A61N 2007/0065; A61B 17/225
See application file for complete search history.

(56) References Cited

U.S. PATENT DOCUMENTS

| | | | |
|---|---|---|---|
| 3,613,069 | A | 10/1971 | Cary |
| 3,735,764 | A | 5/1973 | Balev |
| 3,769,963 | A | 11/1973 | Goldman |
| 3,942,531 | A | 3/1976 | Hoff |
| 4,005,314 | A | 1/1977 | Zinn |
| 4,311,147 | A | 1/1982 | Hausler |
| 4,715,376 | A | 12/1987 | Nowacki et al. |
| 4,858,597 | A | 8/1989 | Kurtze et al. |
| 4,896,673 | A | 1/1990 | Rose et al. |
| 4,905,671 | A | 3/1990 | Senge |
| 4,962,752 | A | 10/1990 | Reichenberger et al. |
| 4,979,501 | A | 12/1990 | Valchanov et al. |
| 5,009,232 | A | 4/1991 | Hassler et al. |
| 5,015,929 | A | 5/1991 | Cathignol et al. |
| 5,149,406 | A | 9/1992 | Mullen et al. |
| 5,150,713 | A | 9/1992 | Okazaki |
| 5,193,527 | A | 3/1993 | Schafer |
| 5,195,508 | A | 3/1993 | Muller et al. |
| 5,204,820 | A | 4/1993 | Strobel et al. |
| 5,231,976 | A | 8/1993 | Wiksell |
| 5,240,005 | A | 8/1993 | Viebach |
| 5,245,988 | A | 9/1993 | Einars et al. |
| 5,259,368 | A | 11/1993 | Wiksell |
| 5,284,143 | A | 2/1994 | Rattner |
| 5,304,170 | A | 4/1994 | Green |
| 5,304,207 | A | 4/1994 | Stromer |
| 5,327,890 | A | 7/1994 | Matura et al. |
| 5,360,447 | A | 11/1994 | Koop |
| 5,374,236 | A | 12/1994 | Hassler |
| 5,393,296 | A | 2/1995 | Rattner |
| 5,409,446 | A | 4/1995 | Rattner |
| 5,419,327 | A | 5/1995 | Rohwedder et al. |
| 5,423,803 | A | 6/1995 | Tankovich et al. |
| 5,435,304 | A | 7/1995 | Oppelt et al. |
| 5,458,652 | A | 10/1995 | Uebelacker |
| 5,509,200 | A | 4/1996 | Frankeny et al. |
| 5,529,572 | A | 6/1996 | Spector |
| 5,595,178 | A | 1/1997 | Voss et al. |
| 5,618,275 | A | 4/1997 | Bock |
| 5,658,239 | A | 8/1997 | Delmenico |
| 5,675,495 | A | 10/1997 | Biermann et al. |
| 5,676,159 | A | 10/1997 | Navis |
| 5,709,676 | A | 1/1998 | Alt |
| 5,722,411 | A | 3/1998 | Suzuki |
| 5,790,305 | A | 8/1998 | Marcellin-Dibon et al. |
| 5,827,204 | A | 10/1998 | Grandia et al. |
| 6,013,122 | A | 1/2000 | Klitzman et al. |
| 6,036,661 | A | 3/2000 | Schwarze et al. |
| 6,039,694 | A | 3/2000 | Larson |
| 6,058,932 | A | 5/2000 | Hughes |
| 6,080,119 | A | 6/2000 | Schwarze et al. |
| 6,096,029 | A | 8/2000 | O'Donnell, Jr. |
| 6,113,559 | A | 9/2000 | Klopotek |
| 6,113,560 | A | 9/2000 | Simnacher |
| 6,176,839 | B1 | 1/2001 | Deluis et al. |
| 6,186,963 | B1 | 2/2001 | Schwarze et al. |
| 6,210,329 | B1 | 4/2001 | Christmas |
| 6,309,355 | B1 | 10/2001 | Cain et al. |
| 6,325,769 | B1 | 12/2001 | Klopotek |
| 6,350,245 | B1 | 2/2002 | Cimino |
| 6,368,929 | B1 | 4/2002 | Hill et al. |
| 6,390,995 | B1 | 5/2002 | Ogden et al. |
| 6,450,979 | B1 | 9/2002 | Miwa et al. |
| 6,454,713 | B1 | 9/2002 | Ishibashi et al. |
| 6,487,447 | B1 | 11/2002 | Weimann et al. |
| 6,491,685 | B2 | 12/2002 | Visuri |
| 6,515,842 | B1 | 2/2003 | Hayworth et al. |
| 6,519,376 | B2 | 2/2003 | Biagi et al. |
| 6,551,308 | B1 | 4/2003 | Muller et al. |
| 6,666,834 | B2 | 12/2003 | Restle et al. |
| 6,755,821 | B1 | 6/2004 | Fry |
| 6,800,122 | B2 | 10/2004 | Anderson et al. |
| 6,905,467 | B2 | 6/2005 | Bradley |
| 6,942,663 | B2 | 9/2005 | Vargas et al. |
| 6,948,843 | B2 | 9/2005 | Laugharn et al. |
| 6,972,116 | B2 | 12/2005 | Brill et al. |
| 7,189,209 | B1 | 3/2007 | Ogden et al. |
| 7,250,047 | B2 | 7/2007 | Anderson et al. |
| 7,311,678 | B2 | 12/2007 | Spector |
| 7,364,554 | B2 | 4/2008 | Bolze et al. |
| 7,405,510 | B2 | 6/2008 | Kaminski et al. |
| 7,470,240 | B2 | 12/2008 | Schultheiss et al. |
| 7,507,213 | B2 | 3/2009 | Schultheiss et al. |
| 7,588,547 | B2 | 9/2009 | Deem et al. |
| 7,867,178 | B2 | 1/2011 | Simnacher |
| 7,985,189 | B1 | 7/2011 | Ogden et al. |
| 7,988,631 | B2 | 8/2011 | Bohris |
| 8,057,408 | B2 | 11/2011 | Cain et al. |
| 8,088,073 | B2 | 1/2012 | Simnacher et al. |
| 8,092,401 | B2 | 1/2012 | Schultheiss |
| 8,102,734 | B2 | 1/2012 | Sliwa et al. |
| 8,235,899 | B2 | 8/2012 | Hashiba |
| 8,257,282 | B2 | 9/2012 | Uebelacker et al. |
| 8,298,162 | B2 | 10/2012 | Del Giglio |
| 8,323,220 | B2 | 12/2012 | Babaev |
| 8,343,420 | B2 | 1/2013 | Cioanta et al. |
| 8,357,095 | B2 | 1/2013 | Anderson et al. |
| 8,672,721 | B2 | 3/2014 | Camilli |
| 8,684,970 | B1 | 4/2014 | Koyfman |
| 2002/0009015 | A1 | 1/2002 | Laugharn et al. |
| 2002/0193831 | A1 | 12/2002 | Smith |
| 2003/0167964 | A1 | 9/2003 | Anderson et al. |
| 2003/0233045 | A1 | 12/2003 | Vaezy |
| 2004/0006288 | A1 | 1/2004 | Spector et al. |
| 2004/0181219 | A1 | 9/2004 | Goble et al. |
| 2005/0015023 | A1 | 1/2005 | Ein-Gal |
| 2005/0150830 | A1 | 7/2005 | Laugharn |
| 2006/0036168 | A1 | 2/2006 | Liang et al. |
| 2006/0064082 | A1 | 3/2006 | Bonutti |
| 2006/0100550 | A1† | 5/2006 | Schultheiss |
| 2006/0158956 | A1 | 7/2006 | Laugharn et al. |
| 2006/0173388 | A1 | 8/2006 | Ginter et al. |
| 2006/0184071 | A1 | 8/2006 | Klopotek |
| 2006/0200116 | A1 | 9/2006 | Ferren et al. |
| 2007/0016112 | A1 | 1/2007 | Schultheiss et al. |
| 2007/0038060 | A1 | 2/2007 | Cerwin et al. |
| 2007/0049829 | A1 | 3/2007 | Kaminski et al. |
| 2007/0055180 | A1 | 3/2007 | Deem et al. |
| 2007/0065420 | A1 | 3/2007 | Johnson |
| 2007/0219760 | A1 | 9/2007 | Yang et al. |
| 2007/0239072 | A1 | 10/2007 | Schultheiss et al. |
| 2007/0239082 | A1 | 10/2007 | Schultheiss et al. |
| 2007/0239084 | A1 | 10/2007 | Voss |
| 2007/0249939 | A1 | 10/2007 | Gerbi et al. |
| 2008/0009774 | A1 | 1/2008 | Capelli et al. |
| 2008/0009885 | A1 | 1/2008 | Del Giglio |
| 2008/0021447 | A1 | 1/2008 | Davison et al. |
| 2008/0071198 | A1 | 3/2008 | Ogden et al. |
| 2008/0107744 | A1 | 5/2008 | Chu |
| 2008/0132810 | A1 | 6/2008 | Scoseria et al. |
| 2008/0146971 | A1 | 6/2008 | Uebelacker et al. |
| 2008/0154157 | A1 | 6/2008 | Altshuler et al. |
| 2008/0183200 | A1 | 7/2008 | Babaev |

(56) References Cited

U.S. PATENT DOCUMENTS

| | | | |
|---|---|---|---|
| 2008/0194967 A1 | 8/2008 | Sliwa et al. |
| 2008/0195003 A1 | 8/2008 | Sliwa et al. |
| 2008/0262483 A1 | 10/2008 | Capelli et al. |
| 2008/0269163 A1 | 10/2008 | Sostaric |
| 2008/0269608 A1 | 10/2008 | Anderson et al. |
| 2008/0319356 A1 | 12/2008 | Cain et al. |
| 2009/0018472 A1 | 1/2009 | Soltani et al. |
| 2009/0275832 A1 | 11/2009 | Gelbart |
| 2010/0076349 A1 | 3/2010 | Babaev |
| 2010/0082019 A1 | 4/2010 | Neev |
| 2010/0087899 A1 | 4/2010 | Erez et al. |
| 2010/0168575 A1 | 7/2010 | Hashiba |
| 2010/0204617 A1 | 8/2010 | Ben-Ezra |
| 2010/0208467 A1 | 8/2010 | Dross |
| 2010/0274161 A1 | 10/2010 | Alhari et al. |
| 2010/0280420 A1 | 11/2010 | Barthe et al. |
| 2010/0331741 A9 | 12/2010 | Cioanta et al. |
| 2011/0034832 A1 † | 2/2011 | Cioanta |
| 2011/0087157 A1 | 4/2011 | Cioanta et al. |
| 2012/0157892 A1 | 6/2012 | Reitmajer et al. |
| 2012/0253240 A1* | 10/2012 | Uebelacker ........ A61B 17/2251 601/4 |
| 2012/0253416 A1 | 10/2012 | Erez et al. |
| 2012/0310232 A1 | 12/2012 | Erez |
| 2012/0323147 A1 | 12/2012 | Scheirer |
| 2012/0330288 A1 | 12/2012 | Clementi et al. |
| 2013/0018287 A1 † | 1/2013 | Capelli |
| 2013/0046179 A1 | 2/2013 | Humayun |
| 2013/0046207 A1 | 2/2013 | Capelli |
| 2013/0165824 A1* | 6/2013 | Rubin ................... A61H 1/005 601/46 |
| 2014/0005576 A1 | 1/2014 | Adams |
| 2014/0243715 A1 | 8/2014 | Cioanta et al. |
| 2014/0257144 A1 | 9/2014 | Capelli et al. |
| 2014/0276722 A1 | 9/2014 | Parihar et al. |
| 2014/0277219 A1 | 9/2014 | Nanda |
| 2015/0126913 A1 | 5/2015 | Jurna et al. |
| 2015/0217111 A1 | 8/2015 | Stevenson et al. |
| 2016/0016013 A1 | 1/2016 | Capelli et al. |
| 2016/0067139 A1 | 3/2016 | Katragadda et al. |
| 2016/0271419 A1 | 9/2016 | Varghese et al. |

FOREIGN PATENT DOCUMENTS

| | | |
|---|---|---|
| CN | 101155614 | 4/2008 |
| CN | 100530868 | 8/2009 |
| CN | 101610736 | 12/2009 |
| CN | 102057422 | 5/2011 |
| CN | 102247661 | 11/2011 |
| CN | 105209117 | 12/2015 |
| CN | 105246419 | 1/2016 |
| DE | 3150430 | 7/1983 |
| DE | 3710371 | 10/1988 |
| DE | 60008898 | 1/2005 |
| DE | 102007046902 | 4/2009 |
| EP | 0008647 | 3/1980 |
| EP | 0243650 | 11/1987 |
| EP | 0322473 | 7/1989 |
| EP | 0326620 | 8/1989 |
| EP | 2964326 | 1/2016 |
| EP | 3626307 | 3/2020 |
| FR | 2605874 | 5/1988 |
| JP | S61-293447 | 12/1986 |
| JP | 62-192150 | 8/1987 |
| JP | S63-183050 | 7/1988 |
| JP | 6-7365 | 1/1994 |
| JP | H06-505648 | 6/1994 |
| JP | 8-140984 | 6/1996 |
| JP | H 08140984 | 6/1996 |
| JP | 8-194079 | 7/1996 |
| JP | H 09103434 | 4/1997 |
| JP | H 10192289 | 7/1998 |
| JP | H 10328192 | 12/1998 |
| JP | 2007-000218 | 1/2007 |
| JP | 2009-518126 | 4/2009 |
| RU | 2121812 C1 | 11/1998 |
| RU | 2151559 C1 | 6/2000 |
| TW | I 292341 | 1/2008 |
| TW | I 350249 | 10/2011 |
| WO | WO 91/10227 | 7/1991 |
| WO | WO/02/030256 A2 | 4/2002 |
| WO | WO 2007/067563 | 6/2007 |
| WO | WO 2007/088546 | 8/2007 |
| WO | WO/07/146988 | 12/2007 |
| WO | WO 2008/052198 | 5/2008 |
| WO | WO 2008/074005 | 6/2008 |
| WO | WO 2008/137942 | 11/2008 |
| WO | WO/11/077466 A1 | 6/2011 |
| WO | WO 2011/091020 | 7/2011 |
| WO | WO-2011089270 A1 * | 7/2011 ............... A61N 7/02 |
| WO | WO 2013/012724 | 1/2013 |
| WO | WO 2014/138582 | 9/2014 |
| WO | WO 2014/191263 | 12/2014 |
| WO | WO 2015/176001 | 11/2015 |

OTHER PUBLICATIONS

Extended European Search Report Issued in Corresponding European Patent Application No. 20153807.1, dated Jun. 9, 2020.
International Preliminary Report on Patentability Issued in Corresponding PCT Application No. PCT/US2017/042122, dated Jan. 22, 2019.
International Search Report and Written Opinion Issued in Corresponding PCT Application No. PCT/US2017/042122, dated Jan. 9, 2018.
International Search Report and Written Opinion Issued in Corresponding PCT Application No. PCT/US14/21746, dated Sep. 12, 2014.
Office Action Issued in Corresponding Japanese Patent Application No. 2019-012062, dated Jun. 16, 2020.
Partial Supplementary Search Report Issued in Corresponding European Patent Application No. EP18754679.1, dated Jul. 29, 2020.
Schmitz, et al., "Treatment of Chronic Plantar Fasciopathy with Extracorporeal Shock Waves (Review)," *Journal of Orthopaedic Surgery and Research*, 8(1); 31, 2013.
Ushakov, et al., "Impulse Breakdown of Liquids," New York, New York: Springer. 2007.
Baumler et al., Q-Switch Laser and Tattoo Pigments: First Results of the Chemical and Photophysical Analysis of 41 Compounds, Lasers in Surgery and medicine 26:13-21 (2000), pp. 13-21.
Bickle, "Abdominal X Rays Made Easy: Calcification," Student BMJ Volume, Aug. 10, 2002, 727-274.
Burov, et al., "Nonlinear Ultrasound: Breakdown of Microscopic Biological Structures and Nonthermal Impact on Malignant Tumor," *Doklady Biochemistry and Biophysics*, 383(3), pp. 101-104. (2002).
Chen et al., "The disappearance of ultrasound contrast bubbles: Observations of bubble dissolution and Cavitation nucleation", Ultrasound in Med. & Biol., vol. 28, No. 6, pp. 793-803, 2002.
Delius, et al., "Biological Effects of Shock Waves: Kidney Haemorrhage by Shock Waves in Dogs—Administration Rate Dependence," *Ultrasound Med Biol.*, 14(8), 689-694, 1988.
Eisenmenger, W. et al., "The First Clinical Results of Wide-Focus and Low-Pressure ESWL" Ultrasound in Med. & Biol., vol. 28, No. 6, pp. 769-774, 2002.
Eisenmenger, Wolfgang, "The Mechanisms of Stone Fragmentation in ESWL", Ultrasound in Med. & Biol., vol. 27, No. 5, pp. 683-693, 2001.
Falco, "Single-Point Nonlinearity Indicators for the Propagation of High-Amplitude Acoustic Signals," Ph.D. Thesis, Graduate Program in Acoustics, The Pennsylvania State University, University Park, PA, May 2007.
Fernando, "A Nonlinear Computational Method for the Propagation of Shock Waves in aero-Engine Inlets Towards A New Model for Buzz-Saw Noise Prediction," $15^{th}$ AIAA/CEAS Aerocoustics Conferences ($30^{th}$ AIAA Aeronautics Conference_ May 11-13, 2009, p. 1-18.

(56) References Cited

OTHER PUBLICATIONS

Gillitzer, et al., "Low-Frequency Extracorporeal Shock Wave Lithotripsy Improves Renal Pelvic Stone Disintegration An A Pig Model," *BJU Int*, 176, 1284-1288, 2009.

Ho et al., "Laser-Tattoo Removal—A Study of the Mechanism and the Optimal Treatment Strategy via Computer Simulations", Lasers in Surgery and medicine 30:389-391 (2002).

Kuhn et al., "Impact of extracorporeal shock waves on the human skin with cellulite: A case study of an unique instance", *Clinical Interventions of Aging*, 3(1):201-210, 2008.

Kuperman-Beade et al., "Laser Removal of Tattoos", Am J Clin Dermatol 2001: 2(1):21-25.

Kuzmin et al., "Ultrasonic Cavitational Chemical Technologies", XI Session of the Russian Acoustical Society, Moscow, Nov. 19-23, 2001.

Liu, et al., "Optimized Design of LED Freeform Lens For Uniform Circular Illumination," *Journal of Zhejiang University-Science C*, Computer & Electron, 13(12), 929-936, 2012.

Madbouly, et al., "Slow Versus Fast Shock Wave Lithotripsy Rate for Urolithiasis: A Prospective Randomized Study," *The Journal of Urology*, 173, 127-130, 2005.

Nana, et al., "Application of the Multiple Low-Energy Q-Switched Laser for the Treatment of Tattoos in 21 Cases," China Aesthetic Medicine, 4(21), 621-622, 2012. (English Abstract).

Ng et al., "Therapeutic Ultrasound: Its Application in Drug Delivery", Medicinal Research Reviews, vol. 22, No. 2, 204-223, 2002.

Ogden et al., Principles of Shock Wave Therapy, Clinical Orthopaedics and Related Research, No. 387, pp. 8-17, 2001.

Reichenberger, "Electromagnetic Acoustic Source for Extracorporeal Generation of Shock Waves in Lithotripsy," Siemens Forsch, 1986, 187-194.

Ross et al., "Comparison of Responses of Tattoos to Picosecond and Nanosecond Q-Switched Neodymium: YAG Lasers" ARCH Dermatol/vol. 134, Feb. 1998, pp. 167-171.

Sheth and Pandya, "Melsama: A comprehensive update (Part I)", *Journal of the American Academy of Dermatology*, 65:689-697, 2011.

Sheth and Pandya, "Melsama: A comprehensive update (Part II)", *Journal of the American Academy of Dermatology*, 65:699-714, 2011.

Solis et al., "Experimental Nonsurgical Tattoo Removal in a Guinea Pig Model with Topical Imiquimod and Tretinoin", Dermatol Surg. 2002, 28:83-87.

Timko et al., "In Vitro Quantitative Chemical Analysis of Tattoo Pigments", ARCH Dermatol/vol. 137, Feb. 2001, pp. 143-147.

Varma, S., "Tattoo Ink Darkening of a yellow Tattoo after Q-Switched Laser Treatment", 2002 Blackwell Science Ltd., Clinical and Experimental Dermatology, 27, 461-463.

Vogel, et al., "Shock Wave Emission and Cavitation Bubble Generation by Picosecond and Nanosecond Optical Breakdown in Water," J. Acoust. Soc. Am. 100(1) Jul. 1996.

Wolfrum et al., "Shock wave induced interaction of microbubbles and boundaries", Physics of Fluids, vol. 15, No. 10, Oct. 2003, pp. 2916-2922.

International Search Report and Written Opinion in International Application No. PCT/US2016/032069 dated Aug. 11, 2016.

International Preliminary Report on Patentability in International Application No. PCT/US2016/032069 dated Nov. 23, 2017.

\* cited by examiner
† cited by third party

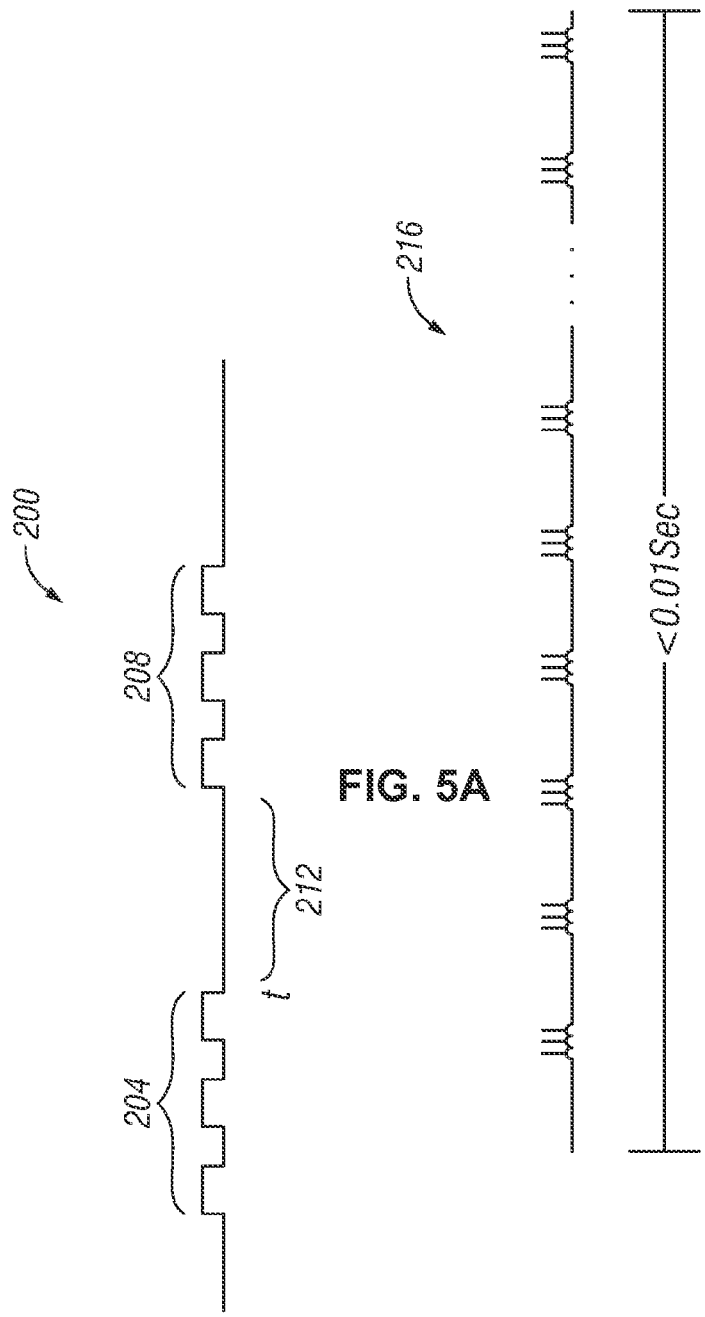

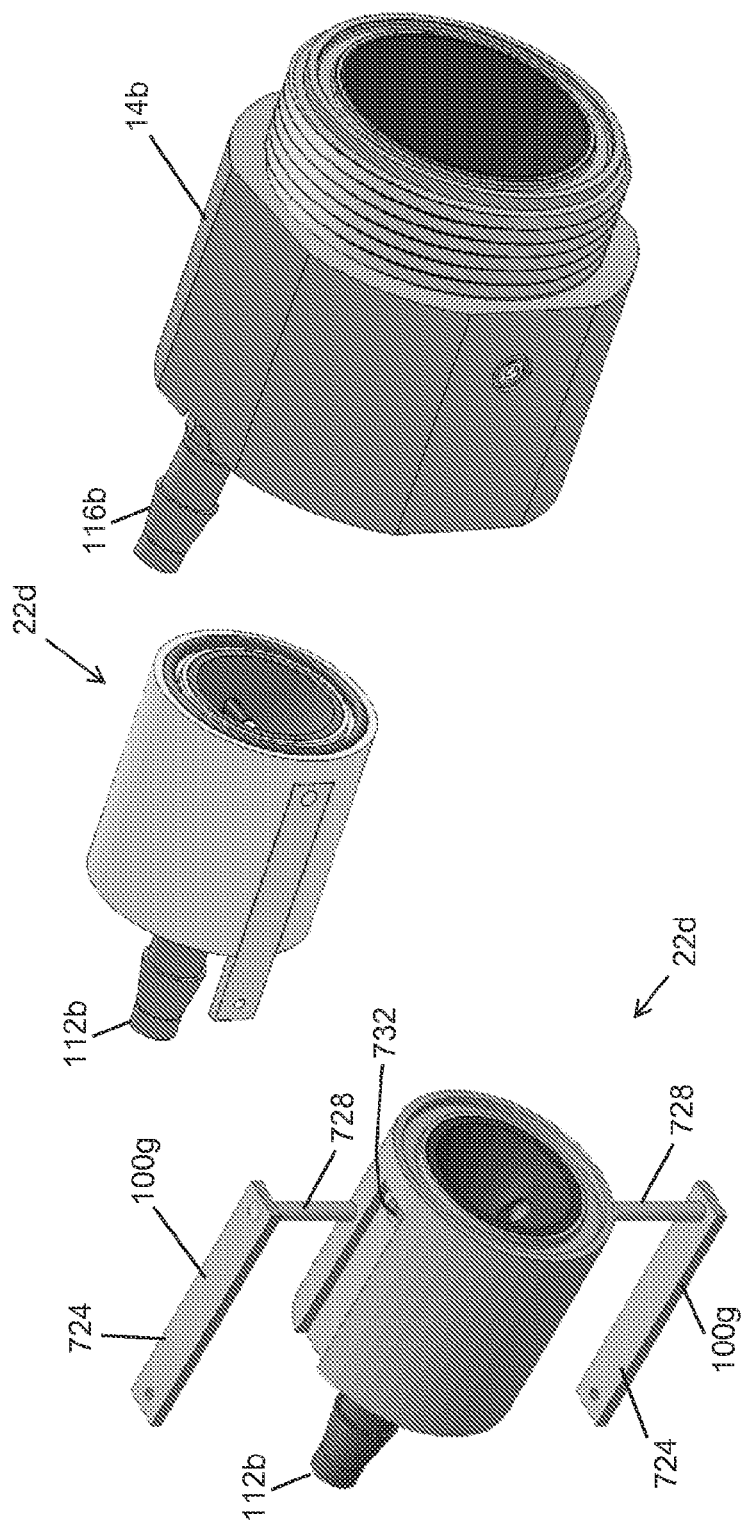

METHODS OF TREATING CELLULITE AND SUBCUTANEOUS ADIPOSE TISSUE

CROSS-REFERENCE TO RELATED APPLICATIONS

This application is a national phase application under 35 U.S.C. 371 of International Application No. PCT/US2016/032069, filed May 12, 2016, which claims priority to U.S. Provisional Patent Application No. 62/160,147, filed May 12, 2015; and U.S. Provisional Patent Application No. 62/277,796, filed Jan. 12, 2016; all of which applications are incorporated by reference in their respective entireties.

BACKGROUND

1. Field of the Invention

The present invention relates generally to methods of treatment for reducing adipose tissue using pressure waves. More particularly, but not by way of limitation, the present invention relates to methods of treatment for reducing subcutaneous adipose tissue using shockwaves.

2. Description of Related Art

Treating Cellulite

Excess body fat, localized adiposity, and cellulite represent important social problems. To date, techniques using radiofrequencies, ultrasound, and carbon dioxide have been studied as treatments for noninvasive body contouring.

Two high intensity ultrasound medical devices products that have been developed for treatment of excess body fat include Ultrashape and LipoSonic. Ultrashape's technology, as disclosed in U.S. Pat. No. 7,347,855 describes "[a] methodology and system for lysing adipose tissue including directing ultrasonic energy at a multiplicity of target volumes within the region, which target volumes contain adipose tissue, thereby to selectively lyse the adipose tissue in the target volumes and generally not lyse non-adipose tissue in the target volumes and computerized tracking of the multiplicity of target volumes notwithstanding movement of the body." "In accordance with a preferred embodiment of the present invention, the modulating provides between 2 and 1000 sequential cycles at an amplitude above a cavitation threshold, more preferably between 25 and 500 sequential cycles at an amplitude above a cavitation threshold and most preferably between 100 and 300 sequential cycles at an amplitude above a cavitation threshold."

Lipsonix's technology, as disclosed in U.S. Pat. No. 7,258,674, describes "a system for the destruction of adipose tissue utilizing high intensity focused ultrasound (HIFU) within a patient's body." Liposonix's high intensity focused ultrasound technology can cause thermal damage of the adipose tissue at focused spots within the adipose tissue.

While both technologies result in adipose tissue destruction, the application of these technologies is likely to have potential safety issues because of the cavitation or thermal affects. These cavitation or thermal affects may even cause damage to non-adipose cells and tissues. Given these safety issues, great care must be taken in treating a patient using these technologies.

An approach to fat tissue volume reduction, that minimizes the safety issues related to these high intensity ultrasound technologies, is cryolipolysis. As the name implies, cryolipolysis is a medical treatment to reshape body contours that relies on controlled cooling of the patient's tissue to cause a non-invasive local reduction of fat deposits. This technology has been commercialized by Zeltiq under the name CoolSculpting and is described in U.S. Pat. No. 8,840,608, entitled, "Methods and devices for selective disruption of fatty tissue by controlled cooling" As described in this patent, the "invention relates to methods for use in the selective disruption of lipid-rich cells by controlled cooling."

While the process is not fully understood, it appears fatty tissue that is cooled below body temperature, but above freezing, undergoes localized cell death followed by a local adipose inflammatory response. This inflammation, over the course of several months, results in a reduction of the fatty tissue layer. See Manstein et al. Specifically, as discussed by Krueger N, et al.: "cryolipolysis exploits the premise that adipocytes are more susceptible to cooling than other skin cells." "Precise application of cold temperatures triggers the death of adipocytes that are subsequently engulfed and digested by macrophages." "An inflammatory process stimulated by apoptosis of adipocytes, as reflected by an influx of inflammatory cells, can be seen within 3 days after treatment and peaks at approximately 14 days thereafter as adipocytes become surrounded by his histiocytes, neutrophils, lymphocytes, and other mononuclear cells."

In terms of efficacy, cryolipolysis has demonstrated reducing adipose tissue by 20-30% in published studies. More importantly, compared to ultrasound technologies based on cavitation or thermal mechanism of action to reduce adipose volume, cryolipolysis is relatively safe. According to Zeiteq's company website, "the controlled cooling of the CoolSculpting procedure targets and eliminates only fat cells. Other treatment modalities, such as lasers, radiofrequency and focused ultrasound, affect fat cells and may affect other adjacent tissue in a way that is not comparable to the CoolSculpting method of Cryolipolysis®." While side effects such as transient local redness, bruising and numbness of the skin are common following the cryolipolysis treatment, the company claims the these side effects typically subside over time.

While the use of cryolipolysis to induce an inflammatory response that results in an adipose tissue volume reduction is an improvement over prior art approaches, it is still less than ideal.

One problem with using cryolipolysis to induce inflammation is the time it takes to administer the cryolipolysis treatment (i.e., cooling the adipose tissue). Typically, the cryolipolysis procedure (e.g. using Coolsculpting) lasts approximately 1-2 hours for each treatment site (e.g., right or left love handle). If a patient seeking to have fat volume reduction in an extensive area, the patient would be required to have multiple 1-2 hour cryolipolysis treatments that could require multiple doctor visits. Another problem, during these long cryolipolysis treatments, the patient is limited on making any movements, which makes the treatment unpleasant. Additionally, a major problem for the physician or spa owner who is treating the patient, the required long treatments limits the throughput of patients that can be seen which has a real impact on the practice revenues.

Approaches to improve cryolipolysis, by use of ultrasound, have been reported. US Patent Application No. 2013/0190744 by Anderson R R., one on the primary inventors of cryolipolysis, discloses, "cooling of the lipid-rich tissue can be accompanied by mechanical or other disruption of the fatty tissue, e.g., through application of acoustic fields that may be either constant or oscillating in time. For example, one or more transducers may be introduced into the region of tissue being cooled through the catheter, and signals provided to them to produce mechanical oscillations and disruption of the fatty tissue." "Alternatively, ultrasound energy can be provided from one or more sources of such energy, e.g., piezoelectric transducers, provided in contact with an outer surface of the subject's body during the cooling procedure. Such ultrasound energy can optionally be focused to the approximate depth of the fatty tissue being cooled to further disrupt the tissue."

Another group, lead by Ferraro G A, studied synergistic effects of cryolipolysis and shockwaves for noninvasive body contouring. This technology developed by the Promoitalia Group SP and called Ice-Shock Lipolysis, "is a new noninvasive procedure for reducing subcutaneous fat volume and fibrous cellulite in areas that normally would be treated by liposuction." Ice-Shock Lipolysis "uses a combination of acoustic waves and cryolipolysis. Shockwaves are focused on the collagen structure of cellulite-afflicted skin. When used on the skin and underlying fat, they cause a remodeling of the collagen fibers, improving the orange-peel appearance typical of the condition. Cryolipolysis, on the other hand, is a noninvasive method used for the localized destruction of subcutaneous adipocytes, with no effects on lipid or liver marker levels in the bloodstream. The combination of the two procedures causes the programmed death and slow resorption of destroyed adipocytes."

The combination of cryolipolysis and acoustic waves promises to improve the outcome of the cryolipolysis procedure. As discussed in the prior art, the use of the acoustic waves are to either aid in the direct disruption of the adipose cell or to provide better appearance outcomes by remodeling the collagen fibers. However, the principal method of inducing inflammation, which leads to the adipose tissue volume reduction, is from the cooling of the adipose tissue. As a result, the fundamental problems, as discussed above, related to the cryolipolysis treatment has not changed.

SUMMARY

Embodiments of the present disclosure are directed to methods of inducing therapeutic adipose tissue inflammation using high frequency pressure waves (e.g. high frequency shockwaves) wherein the inflammation results in a reduction in the volume of subcutaneous adipose tissue. In some embodiments, the high frequency pressure waves (e.g., in the form of shockwaves) are applied to the skin so as to induce lipid nucleation, which can cause crystallization and eventually, adipocyte apoptosis. Adipocyte apoptosis can result in a reduction in the appearance of the cellulite on the skin (e.g., smoother skin) overlying the treated adipocyte tissue. In some embodiments, the applied pressure waves are applied at a rate and magnitude such that minimal to no cavitation occurs in the tissue. In some embodiments, the methods of treatment can reduce undesired side effects and the total times per treatment (TTPT) relative to known systems. Moreover, the present pressure wave therapies can be used to induce inflammation across a given area of adipose tissue such that a practical total time per treatment (TTPT) can be obtained.

Present embodiments include methods that comprise: generating a plurality of pressure waves at sub-cavitation levels and delivering at least a portion of the plurality of pressure waves to an adipose tissue thereby inducing inflammation in the adipose tissue. It is noted that throughout the application, pressure waves are understood to include shockwaves.

Some embodiments include methods that comprise: generating a plurality of pressure waves at a pulse rate of at least 10 Hz and delivering to an adipose tissue at least a portion of the plurality of pressure waves.

Some embodiments include methods of applying electrohydraulic generated shockwaves to induce inflammation in an adipose tissue. The EH-shockwave systems utilized can be configured to deliver shockwaves to tissues to induce inflammation on the treated tissue, such as by delivering shockwaves at higher frequencies (e.g., greater than ~10 Hz).

Still other embodiments also include methods of generating pressure wave energy of at least 0.5 mJ per $mm^2$ at the pressure wave outlet window and delivering to an adipose tissue at least a portion of the plurality of pressure waves. In further embodiments, the pressure wave energy of at least 0.5 mJ per $mm^2$ at the pressure wave outlet window is applied to at least a 20 $mm^2$ area. In some embodiments, at least a portion of the generated pressure waves are planar or unfocused.

Some embodiments include a method of treating a patient to reduce subcutaneous fat in a treatment area. The fat comprises fat cells having intracellular fat and interstitial space between the fat cells. The method can comprise directing a pressure wave generating probe to expose an external area of the patient to a series of pressure waves, where the pressure wave generating probe comprises a pressure wave outlet window, where the pressure wave generating probe emits at least 0.5 mJ per $mm^2$ at the pressure wave outlet window, and where the pressure waves are not focused prior to entering into the treatment area of the patient.

Some embodiments include a method of inducing inflammation of subcutaneous adipose tissue. The method can comprise directing a pressure wave generating probe to expose an external area of the patient to a series of pressure waves, where the pressure wave generating probe comprises a pressure wave outlet window and where the pressure wave generating probe emits at least 0.5 mJ per $mm^2$ of the pressure wave outlet window.

Some embodiments include a method of applying pressure wave energy to an adipose tissue. The method can comprise directing a pressure wave generating probe to expose an external area of the patient to a series of pressure waves, where the pressure wave generating probe comprises a pressure wave outlet window and where the pressure wave generating probe emits at least 0.5 mJ per $mm^2$ of the pressure wave outlet window.

Some embodiments include a method of treating a patient to reduce the appearance of cellulite in a treatment area. The method can comprise directing a pressure wave generating probe to expose an external area of the patient to a series of pressure waves, where the pressure wave generating probe comprises a pressure wave outlet window and where the pressure wave generating probe emits at least 0.5 mJ per $mm^2$ of the pressure wave outlet window.

Some embodiments include a method of inducing inflammation in subcutaneous adipose tissue. The method can comprise directing a pressure wave generating probe to expose an external area of the patient to a series of pressure waves, where the pressure wave generating probe comprises a pressure wave outlet window and where the probe is emits a series of pressure waves that would not induce transient cavitation bubbles in an aqueous solution.

Some embodiments include a method where the probe emits a series of pressure waves that would induce minimal to no adipose cell damage while treating an external treatment area of a subject, e.g., a patient or animal model. For example, in some embodiments, the probe emits a series of pressure waves that would increase the amount of lipid crystals within an adipose tissue within the treatment area of the subject as compared with an adipose tissue sample outside of the treatment area of the subject. In some embodiments, the probe can emit a series of pressure waves that would cause a comparable increase of a luminosity value of an adipose tissue sample from the treated area relative to that of an adipose tissue sample from an untreated area of the subject. In still other embodiments, the probe emits a series of pressure waves that would cause a comparable volume loss of a treatment area relative to an untreated area of the subject.

The term "coupled" is defined as connected, although not necessarily directly, and not necessarily mechanically; two items that are "coupled" may be unitary with each other. The terms "a" and "an" are defined as one or more unless this disclosure explicitly requires otherwise. The term "substantially" is defined as largely but not necessarily wholly what is specified (and includes what is specified; e.g., substantially 90 degrees includes 90 degrees and substantially parallel includes parallel), as understood by a person of ordinary skill in the art. In any disclosed embodiment, the terms "substantially," "approximately," and "about" may be substituted with "within [a percentage] of" what is specified, where the percentage includes 0.1, 1, 5, and 10 percent.

The terms "comprise" (and any form of comprise, such as "comprises" and "comprising"), "have" (and any form of have, such as "has" and "having"), "include" (and any form of include, such as "includes" and "including") and "contain" (and any form of contain, such as "contains" and "containing") are open-ended linking verbs. As a result, a system or apparatus that "comprises," "has," "includes" or "contains" one or more elements possesses those one or more elements, but is not limited to possessing only those elements. Likewise, a method that "comprises," "has," "includes" or "contains" one or more steps possesses those one or more steps, but is not limited to possessing only those one or more steps.

Any embodiment of any of the present systems, apparatuses, and methods can consist of or consist essentially of—rather than comprise/include/contain/have—any of the described steps, elements, and/or features. Thus, in any of the claims, the term "consisting of" or "consisting essentially of" can be substituted for any of the open-ended linking verbs recited above, in order to change the scope of a given claim from what it would otherwise be using the open-ended linking verb.

Further, a structure (e.g., a component of an apparatus) that is configured in a certain way is configured in at least that way, but it can also be configured in other ways than those specifically described.

Details associated with the embodiments described above and others are presented below.

BRIEF DESCRIPTION OF THE DRAWINGS

The following drawings illustrate by way of example and not limitation. For the sake of brevity and clarity, every feature of a given structure is not always labeled in every figure in which that structure appears. Identical reference numbers do not necessarily indicate an identical structure. Rather, the same reference number may be used to indicate a similar feature or a feature with similar functionality, as may non-identical reference numbers. The figures are drawn to scale (unless otherwise noted), meaning the sizes of the depicted elements are accurate relative to each other for at least the embodiment depicted in the figures.

FIGS. 5A-5B depict a timing diagrams of one example of the timed application of energy cycles or voltage pulses in the system of FIG. 3 and/or the handheld probe of FIG. 4.

FIGS. 12A and 12B depict parts of the assembly of the probe of FIG. 11.

DESCRIPTION OF ILLUSTRATIVE EMBODIMENTS

Figure 1:
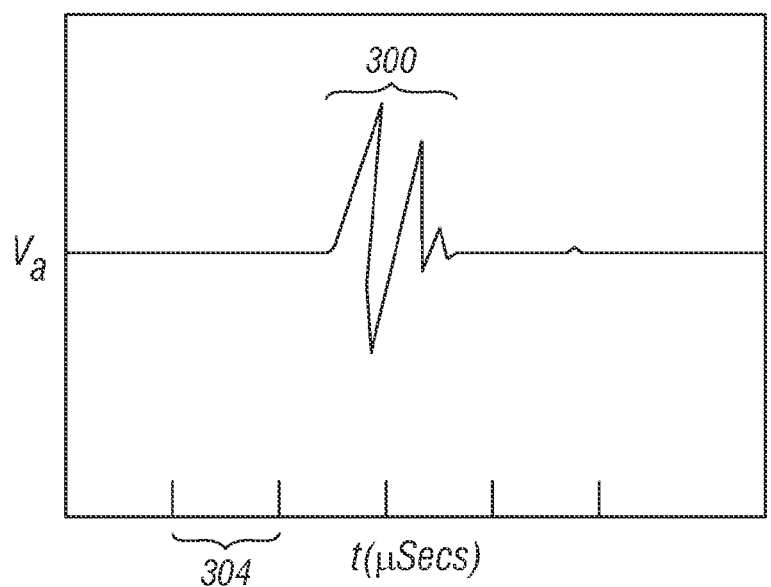
FIG. 1 depicts a waveform that can be emitted by system of FIG. 3 and/or the handheld probe of FIG. 4 into target tissue.

Embodiments of the present disclosure are directed to inducing inflammation in a tissue and particularly a tissue near the surface of the skin such as a subcutaneous adipose tissue, by applying a plurality of shockwaves to the tissue. The induced inflammation will lead to eventual apoptosis to a portion of the cells in the treated area. While the shockwave treatments induce inflammation, the shockwaves are at a strength, frequency, and duration that are not likely to cause cavitation or thermal degradation in the treated tissue. As such, cell rupturing, would not be likely to occur. Rather, apoptosis would be caused by the inflammatory response of the body.

When the cell is exposed to repeated pressure waves within a certain frequency and energy level, sub-lytic injury occurs that induces inflammation. More particularly, the repeated high frequency, pressure wave energy applied to cells with lipid reserves can cause sub-lytic injury to the lipid containing vacuoles, triggering an inflammatory response. The ability to induce inflammation is dependent on four factors: (1) applied intensity (Pa), (2) the rate of wave pulses (Hz), (3) wave form shape (e.g., wave front rise time (ns) and wave length (ns)), or (4) duration of exposure. One or more of these factors can be manipulated to cause a tissue with a high amount of stored lipids to have increased inflammation as compared to a non-treated area of similar character. The inflammation will eventually result in apoptosis and a reduction in the number of cells in the treated area.

A possible theory to explain the phenomenon of the induced inflammations is the formation of lipid crystals in a sub-cellular structure. In a liquid lipid media, such as in adipose cells, a series of pressure waves at a high frequency may induce nucleation of lipid crystals leading to the formation of crystals sufficiently large to cause injury to cellular organelles, such as a bilayer membrane. This injury initiates an inflammatory response that will eventually lead to apoptosis and necrosis. Nearby cells that are also exposed but not lipid rich like adipocyte cells, such as cells in the epidermis layer, are less likely to be damaged in the process.

In some embodiments, a method of treating a patient to reduce subcutaneous fat in a treatment area can comprise: directing a pressure wave generating probe (such as probe 38 or 38a described below) to expose an external area of the patient to a series of pressure waves, where the pressure wave generating probe comprises a pressure wave outlet window, where the pressure wave generating probe is configured to generate at least 0.5 mJ per mm$^2$ or at least 2 mJ per mm$^2$ at the pressure wave outlet window. For example, the pressure waves can have 0.5, 0.6, 0.8, 0.9, 1, 1.2, 1.4, 1.6, 1.8, 2, 2.2, 2.4, 2.6, 2.8, 3, 3.4, 3.8, 4, 4.4, 4.8, 5, 5.5, 6, 6.5, 7 mJ per mm$^2$, or any value or range therebetween. In some embodiments, the pressure wave generating probe is configured to generate or generates between 0.5 mJ per mm$^2$ to 5 mJ per mm$^2$. In some embodiments, the pressure wave outlet window has an area of 0.5 cm$^2$ to 20 cm$^2$. For example, the outlet window can have an area of at least 0.5, 0.8, 1, 2, 3, 4, 5, 6, 7. 8, 9, 10, 11, 12, 13, 14, 15, 16, 17, 18, 19, 20 cm$^2$, or any value or range therebetween.

In some embodiment, the pressure waves are unfocused or substantially planar prior to entering into the treatment area of the patient. Other embodiments of the present methods comprise focusing the one or more pressure waves to a treatment area. In some embodiments the adipose tissue at which the one or more pressure waves is focused is the depth at which there is adipose tissue. Focusing the shockwaves may result in higher pressures at targeted cells than unfocused or planar waves.

In some embodiments, the treatment area is a portion of butt, thigh, stomach, waist, and/or upper arm area. In some embodiments, the treatment area of subcutaneous fat is within a depth of 0-6 cm from the external area, such as 1, 2, 3, 4, 5, 6 cm, or any value or range therebetween. In some embodiments, the treatment area is at a depth of 1-4 cm.

In some embodiments, the pressure wave directed to the treatment area is a shockwave. FIG. 1 depicts a waveform of a shockwave that can be emitted from a probe and into a volume of tissue. The depicted form can be useful for inducing inflammation without causing cell rupturing. Pulse 300 is of a typical shape for an impulse generated by the described electrohydraulic (EH) spark heads described below. For example, pulse 300 has a rapid rise time (or wave front rise time), a short duration, and a ring down period. The units of vertical axis $V_a$ are arbitrary as may be displayed on an oscilloscope.

In some embodiments, the pressure wave generating probe can emit a shockwave comprising the following waveform characteristics in a transmitting medium. A transmitting medium can be a gas (e.g., air), a tissue (e.g., an adipose tissue) or an aqueous solution (e.g., a saline solution, such as one at 0.5-10% concentration). In some embodiments, a shockwave emitted at the outlet window of the probe and/or delivered to the treatment area can have a shockwave front rise time of less than 20 ns, less than 18 ns, less than 15 ns, or less than 12 ns as measured in a transmitting medium. In some embodiments, the actual acoustic pulse amplitude emitted may be 0.5 to 50 MPa. In some embodiments, the individual time periods 304 may be 0.5 to 50 micro-seconds each in a transmitting medium. In some embodiments, the probe emits a pressure wave at a pulse rate of at least 10 Hz. For example, the probe emits a pressure wave at a pulse rate of between 10 Hz and 1000 Hz., such as 20, 30, 40, 50, 60, 70, 80 90, 100, 150, 200, 250, 300, 350, 400, 450, 500, 550, 600, 650, 700, 750, 800, 850, 900, 950, 1000 Hz, or any value or range therebetween. In some embodiments, the probe emits a pressure wave at a pulse rate of between 10 Hz and 100 Hz. In some embodiments, the probe emits a pressure wave at a pulse rate of between 20 Hz and 75 Hz. In some embodiments, the probe emits a pressure wave at a pulse rate of between 100 Hz and 500 Hz. In some embodiments, the probe emits a pressure wave at a pulse rate of between 500 Hz and 1000 Hz. In some embodiments, the emitted waves are configured according to the characteristics above to induce minimal to no detectable transient cavitation in a transmitting medium.

In some embodiments, the method of treatment induces lipid crystallization, induces inflammation in the treated adipose tissue, reduces the amount of subcutaneous fat in the treatment area, and/or reduces the appearance of cellulite (e.g., resulting in a smoother appearance in the skin overlying the treatment area). In some embodiments, subcutaneous fat comprises fat cells having intracellular fat and interstitial space between the fat cells. A reduction in the amount of fat (e.g., a reduction in volume) can be determined by a histological evaluation or 3-D camera. Example 2 describes a method for detecting a change in adipose tissue volume. In some embodiments, the amount of fat is reduced about 1-14 days after one or more treatments, such as after 1, 2, 3, 4, 5, 6, 7, 8, 9, 10, 11, 12, 13, 14 days after the last treatment, or any value or range therebetween. In some embodiments, an inflammation increase is indicated by an increase of one or more cytokines, such as one or more of leptin, IL-6, and TNF-α, in the patient's blood serum, or in the treatment area after treatment. In some embodiments, an inflammation increase is indicated by an increase in inflammatory cells in the treatment area after treatment. In some embodiments, even with an inflammation increase, the series of pressure waves would induce minimal to no adipose cell rupturing immediately after treatment, such as when treating an external treatment area of an animal model. Cell rupturing can be detected histologically, such as under 200× to 1000× magnification. In some embodiments, inducing lipid crystallization is indicated by relatively higher tissue luminosity value under cross-polarized microscopy as compared with a control sample. Example 3 describes a method for detecting a comparable increase in lipid crystallization. Because of the recognized difficulty of performing such evaluations on a human patient, in some embodiments, the result of a treatment on a human can be estimated to correspond to the result of a treatment protocol on an animal model, such as a minipig.

Inducing crystallization of lipids using the methods of this invention can occur in relatively short treatment times. As a result, the long treatment times seen with the prior art, along with the problems associated with these long treatment times (e.g., office space, costs, discomfort, etc.) can be avoided using this invention. For example, in some embodiments, a treatment session can be 1 to 30 minutes within a 24 hour period. A treatment session can be 1, 2, 4, 5, 8, 10, 12, 15, 18, 20, 22, 24, 26, 28, 30 minutes or any value or within any range therebetween. A treatment session can be performed daily, every other day, every three days, weekly, bi-weekly, monthly, bi-monthly, and quarterly. A treatment plan can comprise 1 to 20 sessions within a one-year period, such as 1, 2, 3, 4, 5, 6, 7, 8, 9, 10, 11, 12, 13, 14, 15, 16, 17, 18, 19, 20 sessions or any value therebetween. In some embodiments, a treatment plan comprises a session at least once per two weeks for at least 6 weeks.

Figure 2:
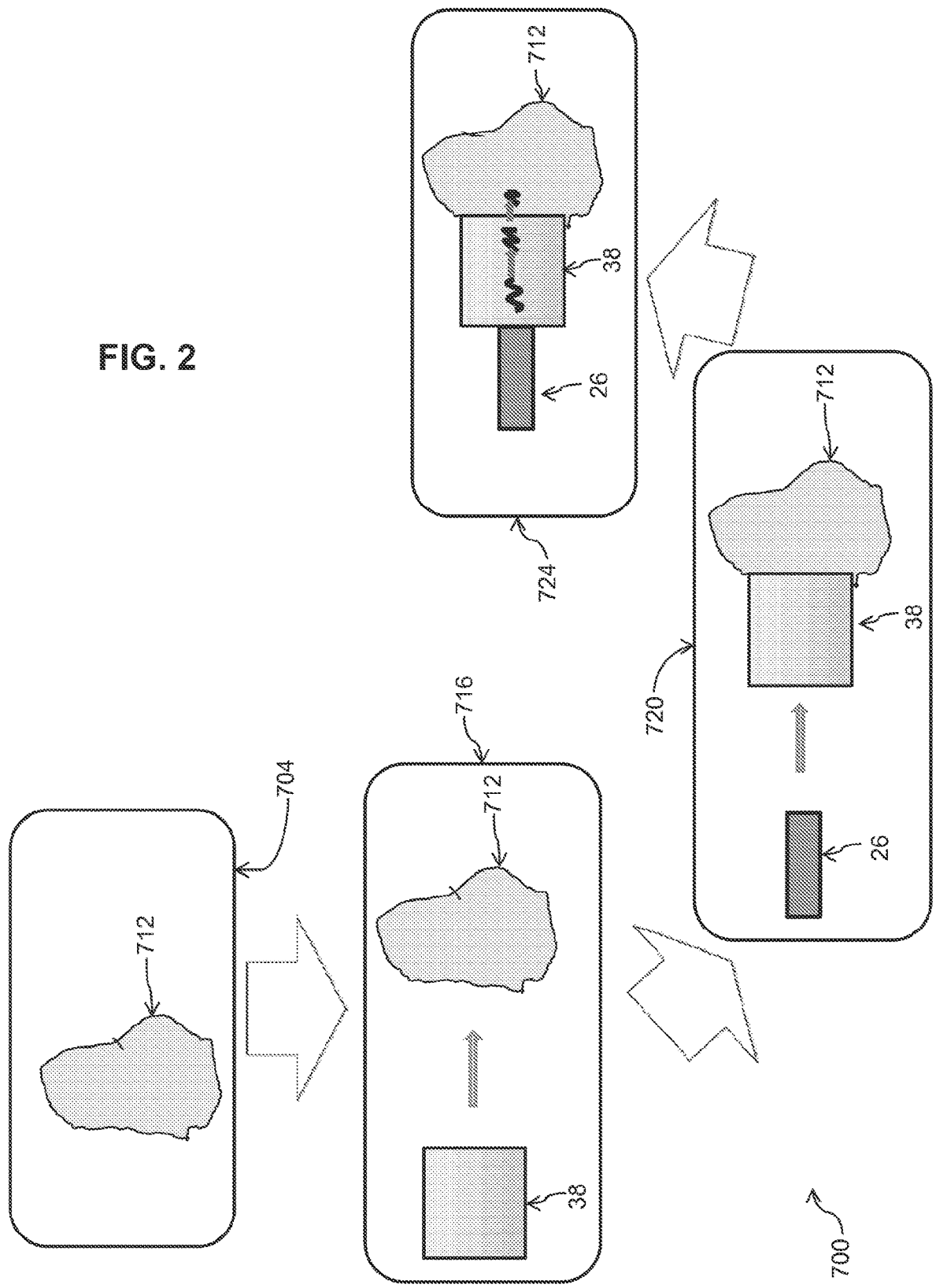
FIG. 2 depicts a conceptual flowchart of one embodiment of the present methods.

FIG. 2 illustrates one embodiment of a method 700 to direct shockwaves to target tissue. In the embodiment shown, method 700 comprises a step 704 in which a treatment area 712 is identified. For example, treatment area 712 can comprise skin affected with cellulite or having an unwanted accumulation of subcutaneous fat. In the embodiment shown, method 700 also comprises a step 716 in which a probe or handpiece 38 is disposed toward treatment area 712, such that shockwaves originating in probe 38 can be directed toward the adipose tissue in the treatment area. In the embodiment shown, method 700 also comprises a step 720 in which a pulse-generation system 26 is coupled to probe 38. In the embodiment shown, method 700 also comprises a step 724 in which pulse-generation system 26 is activated to generate sparks across electrodes within probe 38 to generate shockwaves in probe 38 for delivery to adipose tissue underlying treatment area 712, as shown.

Shockwave Generator

The above-described modalities may employ a shockwave generator. The generator can be configured to deliver focused, defocused, or planar waves with the above-described characteristics. In some embodiments, EH waves are generated. For example, the systems and apparatus described in U.S. Patent Publication No. 2014/0257144 can be configured to apply EH shockwaves at the described rate, energy level, and duration. In particular, the shockwave generating apparatus can be configured to generate a planar or defocused pressure wavefront.

Figure 3:
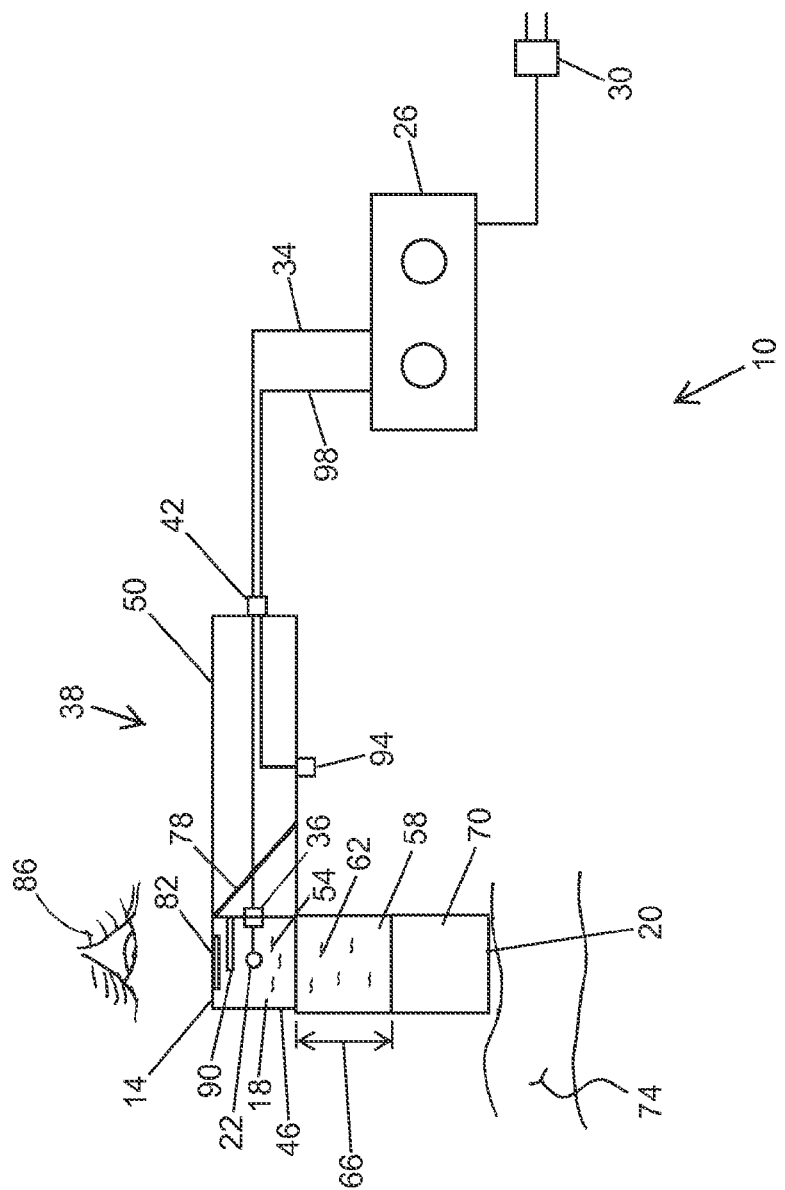
FIG. 3 depicts a block diagram of a first embodiment of the present electro-hydraulic (EH) shockwave generating systems.

With reference to FIG. 3, such a system can include a handheld probe (e.g., with a first housing, such as in FIG. 4) and a separate controller or pulse-generation system (e.g., in or with a second housing coupled to the handheld probe via a flexible cable or the like). In the embodiment shown, apparatus 10 comprises: a housing 14 defining a chamber 18 and a shockwave outlet 20; a liquid (54) disposed in chamber 18; a plurality of electrodes (e.g., in spark head or module 22) configured to be disposed in the chamber to define one or more spark gaps; and a pulse-generation system 26 configured to apply voltage pulses to the electrodes at a rate of between 10 Hz and 1000 Hz, such as between 10 Hz and 100 Hz, 100 Hz and 500 Hz, or 500 Hz and 1000 Hz. In this embodiment, the pulse-generation system 26 is configured to apply the voltage pulses to the electrodes such that portions of the liquid are vaporized to propagate shockwaves through the liquid and the shockwave outlet window.

In the embodiment shown, pulse-generation system 26 is configured for use with an alternating current power source (e.g., a wall plug). For example, in this embodiment, pulse-generation system 26 comprises a plug 30 configured to be inserted into a 110V wall plug. In the embodiment shown, pulse-generation system 26 comprises a capacitive/inductive coil system, on example of which is described below with reference to FIG. 7. In the embodiment shown, pulse-generation system 26 is (e.g., removably) coupled to the electrodes in spark head or module 22 via a high-voltage cable 34, which may, for example, include two or more electrical conductors and/or be heavily shielded with rubber or other type of electrically insulating material to prevent shock. In some embodiments, high-voltage cable 34 is a combined tether or cable that further includes one or more (e.g., two) liquid lumens through which chamber 18 can be filled with liquid and/or via which liquid can be circulated through chamber 18 (e.g., via combined connection 36). In the embodiment shown, apparatus 10 comprises a handheld probe or handpiece 38 and cable 34 is removably coupled to probe 38 via a high-voltage connector 42, which is coupled to spark head or module 22 via two or more electrical conductors 44. In the embodiment shown, probe 38 comprises a head 46 and a handle 50, and probe 38 can comprise a polymer or other electrically insulating material to enable an operator to grasp handle 50 to position probe 38 during operation. For example, handle 50 can be molded with plastic and/or can be coated with an electrically insulating material such as rubber.

In the embodiment shown, a liquid 54 (e.g., a dielectric liquid such as distilled water) is disposed in (e.g., and substantially fills) chamber 18. In this embodiment, spark head 22 is positioned in chamber 18 and surrounded by the liquid such that the electrodes can receive voltage pulses from pulse-generation system 26 (e.g., at a rate of between 10 Hz and 1000 Hz, 10 Hz and 100 Hz, 100 Hz and 500 Hz, or 500 Hz and 1000 Hz) such that portions of the liquid are vaporized to propagate shockwaves through the liquid and shockwave outlet 20. In the embodiment shown, probe 38 includes an acoustic delay chamber 58 between chamber 18 and outlet 20. In this embodiment, acoustic delay chamber is substantially filled with a liquid 62 (e.g., of the same type as liquid 54) and has a length 66 that is sufficient to permit shockwaves to form and/or be directed toward outlet 20. In some embodiments, length 66 may be between 2 millimeters (mm) and 25 millimeters (mm). In the embodiment shown, chamber 18 and acoustic-delay chamber 58 are separated by a layer of sonolucent (acoustically permeable or transmissive) material that permits pressure waves or, more particularly, shockwaves to travel from chamber 18 into acoustic-delay chamber 58. In other embodiments, liquid 62 may be different than liquid 54 (e.g., liquid 62 may comprise bubbles, water, oil, mineral oil, and/or the like). Certain features such as bubbles may introduce and/or improve a nonlinearity in the acoustic behavior of liquid 54 to increase the formation of shockwaves. In further embodiments, chamber 18 and acoustic-delay chamber 58 may be unitary (i.e., may comprise a single chamber). In further embodiments, acoustic-delay chamber 58 may be replaced with a solid member (e.g., a solid cylinder of elastomeric material such as polyurethane). In the embodiment shown, probe 38 further includes an outlet member 70 removably coupled to the housing at a distal end of the acoustic delay chamber, as shown. Member 70 is configured to contact an external area located above tissue 74, and can be removed and either sterilized or replaced between patients. Member 70 comprises a polymer or other material (e.g., low-density polyethylene or silicone rubber) that is acoustically permeable to permit shockwaves to exit acoustic-delay chamber 58 via outlet 20. In some embodiments, an acoustic coupling gel (not shown) may be disposed between member 70 and tissue 74 to lubricate and provide additional acoustic transmission into tissue 74.

In the embodiment shown, probe 38 includes an acoustic mirror 78 that comprises a material (e.g., glass) and is configured to reflect a majority of sound waves and/or shockwaves that are incident on the acoustic mirror. As shown, acoustic mirror 78 can be angled to reflect sound waves and/or shockwaves (e.g., that originate at spark head 22) toward outlet 20 (via acoustic-delay chamber) in a defocused manner. In the embodiment shown, housing 14 can comprise a translucent or transparent window 82 that is configured to permit a user to view (through window 82, chamber 18, chamber 58, and member 70) a region of a patient (e.g., tissue 74) comprising target cells (e.g., during application of shockwaves or prior to application of shockwaves to position outlet 20 at the target tissue). In the embodiment shown, window 82 comprises an acoustically reflective material (e.g., glass) that is configured to reflect a majority of sound waves and/or shockwaves that are incident on the window. For example, window 82 can comprise clear glass of sufficient thickness and strength to withstand the high-energy acoustic pulses produced at spark head 22 (e.g., tempered plate glass having a thickness of about 2 mm and an optical transmission efficiency of greater than 50%).

In FIG. 3, a human eye 86 indicates a user viewing the target tissue through window 82, but it should be understood that target tissue may be "viewed" through window 82 via a camera (e.g., a digital still and/or video camera). By direct or indirect observation, acoustic energy can be positioned, applied, and repositioned according to target tissues, such as a region of cellulite, and by indications of acoustic energy, such as a change in the color of the tissue.

Figure 4:
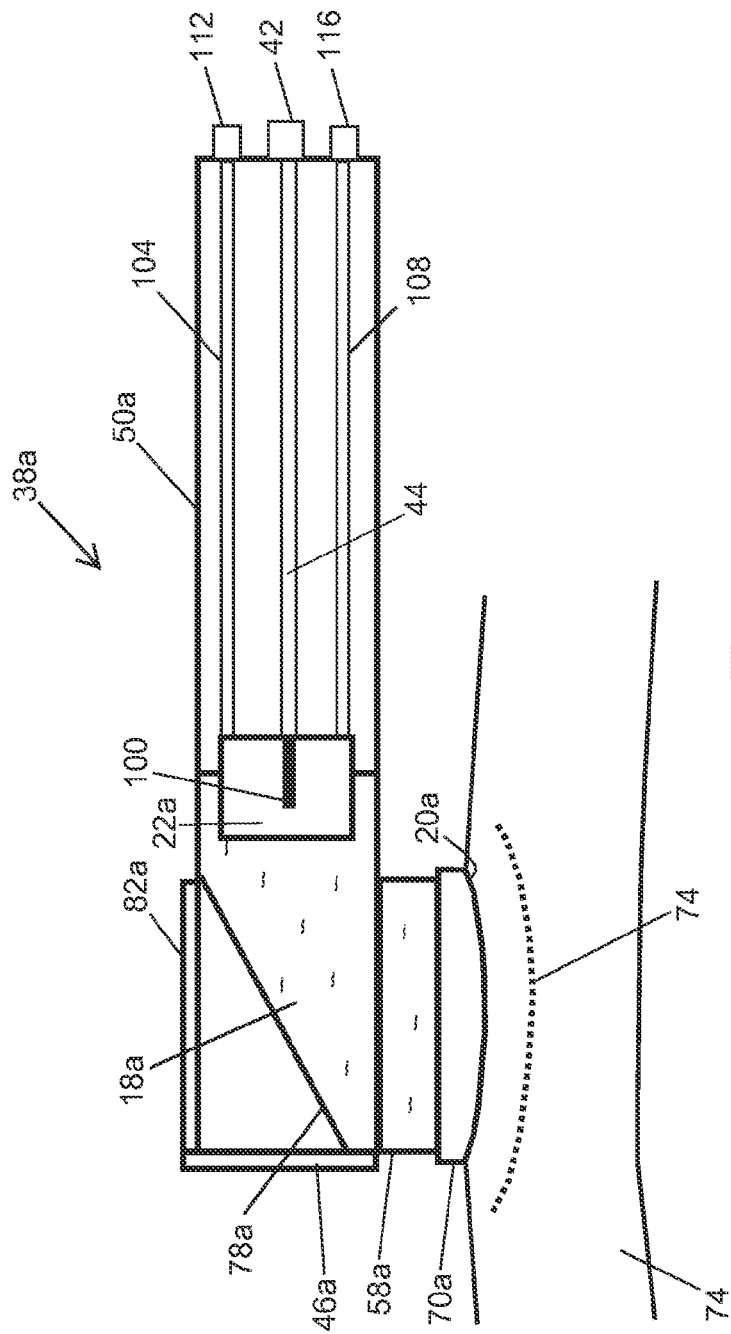
FIG. 4 depicts a cross-sectional side view of a handheld probe for some embodiments of the present EH shockwave generating systems.

FIG. 4 depicts a cross-sectional side view of a second embodiment 38a of the present handheld probes or handpiece for use with some embodiments of the present EH shockwave generating systems and apparatuses. Probe 38a is substantially similar in some respects to probe 38, and the differences are therefore primarily described here. For example, probe 38a is also configured such that the plurality of electrodes of spark head 22a are not visible to a user viewing a region (e.g., of target tissue) through window 82a and outlet 20a. However, rather than including an optical shield, probe 38a is configured such that spark head 22a (and the electrodes of the spark head) are offset from an optical path extending through window 82a and outlet 20a. In this embodiment, acoustic mirror 78a is positioned between spark head 22a and outlet 20a, as shown, to define a boundary of chamber 18a and to direct acoustic waves and/or shockwaves from spark head 22a to outlet 20a. In the embodiment shown, window 82a can comprise a polymer or other acoustically permeable or transmissive material because acoustic mirror 78a is disposed between window 82a and chamber 18a and sound waves and/or shockwaves are not directly incident on window 82a (i.e., because the sound waves and/or shockwaves are primarily reflected by acoustic mirror 78a).

In the embodiment shown, spark head 22a includes a plurality of electrodes 100 that define a plurality of spark gaps. The use of multiple spark gaps can be advantageous because it can double the number of pulses that can be delivered in a given period of time. For example, after a pulse vaporizes an amount of liquid in a spark gap the vapor must either return to its liquid state or must be displaced by a different portion of the liquid that is still in a liquid state. In addition to the time required for the spark gap to be re-filled with water before a subsequent pulse can vaporize additional liquid, sparks also heat the electrodes. As such, for a given spark rate, increasing the number of spark gaps reduces the rate at which each spark gap must be fired and thereby extends the life of the electrodes. Thus, ten spark gaps potentially increases the possible pulse rate and/or electrode life by a factor of ten.

As noted above, high pulse rates can generate large amounts of heat that may increase fatigue on the electrodes and/or increase the time necessary for vapor to return to the liquid state after it is vaporized. In some embodiments, this heat can be managed by circulating liquid around the spark head. For example, in the embodiment of FIG. 4, probe 38 includes conduits 104 and 108 extending from chamber 18a to respective connectors 112 and 116, as shown. In this embodiment, connectors 112 and 116 can be coupled to a pump to circulate liquid through chamber 18a (e.g., and through a heat exchanger. For example, in some embodiments, pulse-generation system 26 (FIG. 3) can comprise a pump and a heat exchanger in series and configured to be coupled to connectors 112 and 116 via conduits or the like. In some embodiments, a filter can be included in probe 38a, in a spark generation system (e.g., 26), and/or between the probe and the spark generation system to filter liquid that is circulated through the chamber As illustrated in FIG. 4, application of each shockwave to a target tissue includes a wave front 118 propagating from outlet 20a and traveling outward through tissue 74. As shown, wave front 118 is curved according to its expansion as it moves outwardly and partially according to the shape of the outer surface of outlet member 70a that contacts tissue 74. In other embodiments, such as that of FIG. 3, the outer shape of the contact member can be planar.

Figure 4A:
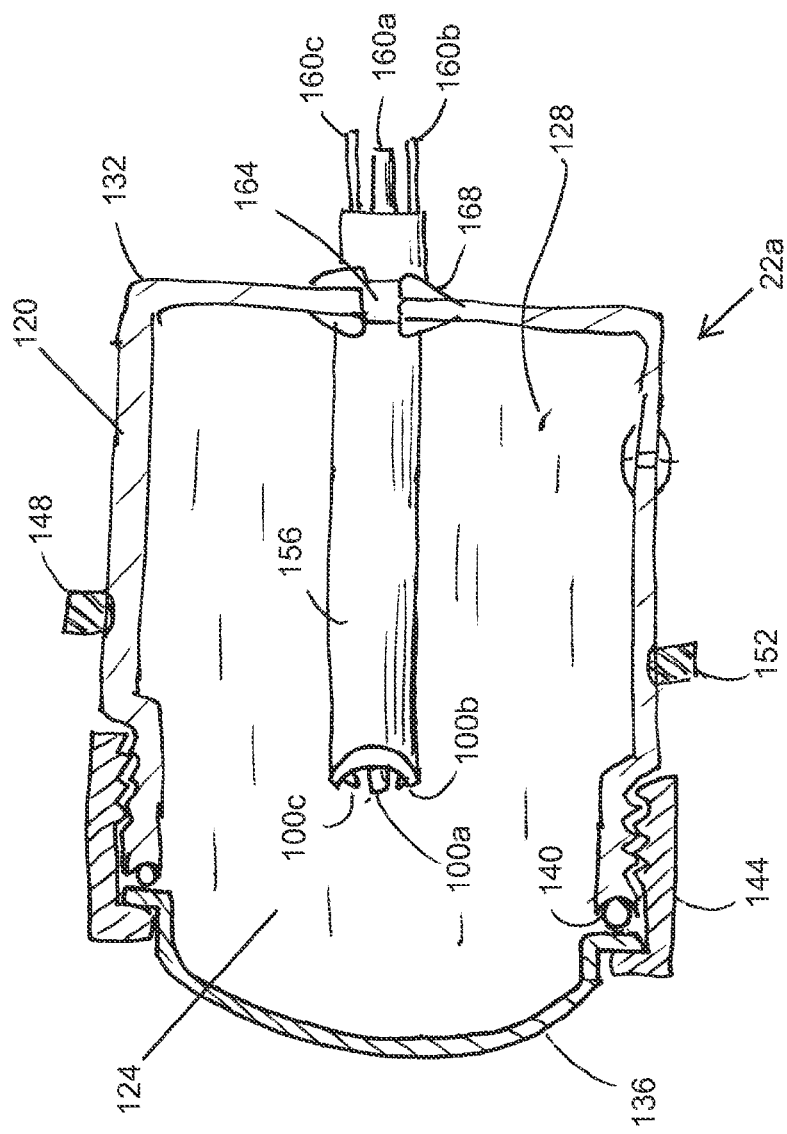
FIG. 4A depicts a cross-sectional side view of a first embodiment of a removable spark head usable with embodiments of the present handheld probes, such as the one of FIG. 4.

FIG. 4A depicts an enlarged cross-sectional view of first embodiment of a removable spark head, shown as module 22a. In the embodiment shown, spark head 22a comprises a sidewall 120 defining a spark chamber 124, and a plurality of electrodes 100a, 100b, 100c disposed in the spark chamber. In the embodiment shown, spark chamber 124 is filled with liquid 128 which may be similar to liquid 54 (FIG. 3). At least a portion of sidewall 120 comprises an acoustically permeable or transmitive material (e.g., a polymer such as polyethylene) configured to permit sound waves and/or shockwaves generated at the electrodes to travel through sidewall 120 and through chamber 18a (FIG. 4). For example, in the embodiment shown, spark head 22a includes a cup-shaped member 132 that may be configured to be acoustically reflective and includes an acoustically permeable cap member 136. In this embodiment, cap member 136 is dome shaped to approximate the curved shape of an expanding wavefront that originates at the electrodes and to compress the skin when applied with moderate pressure. Cap member 136 can be coupled to cup-shaped member 132 with an O-ring or gasket 140 and a retaining collar 144. In the embodiment shown, cup-shaped member 132 has a cylindrical shape with a circular cross-section (e.g., with a diameter of 2 inches or less). In this embodiment, cup-shaped member includes bayonet-style pins 148, 152 configured to align with corresponding grooves in head 46a of probe 38a (FIG. 4) to lock the position of spark head 22a relative to the probe.

In the embodiment shown, an electrode core 156 having conductors 160*a*, 160*b*, 160*c* and extending through aperture 164, with the interface between aperture 164 and electrode core 156 sealed with a grommet 168. In the embodiment shown, a central conductor 160*a* extends through the center of core 156 and serves as a ground to corresponding center electrode 100*a*. Peripheral conductors 160*b*, 160*c* are in communication with peripheral electrodes 100*b*, 100*c* to generate sparks across the spark gap between electrodes 100*a* and 100*b*, and between electrodes 100*a* and 100*c*. It should be understood that while two spark gaps are shown, any number of spark gaps may be used, and may be limited only by the spacing and size of the spark gaps. For example, other embodiments include 3, 4, 5, 6, 7, 8, 9, 10, or even more spark gaps.

Figure 4B:
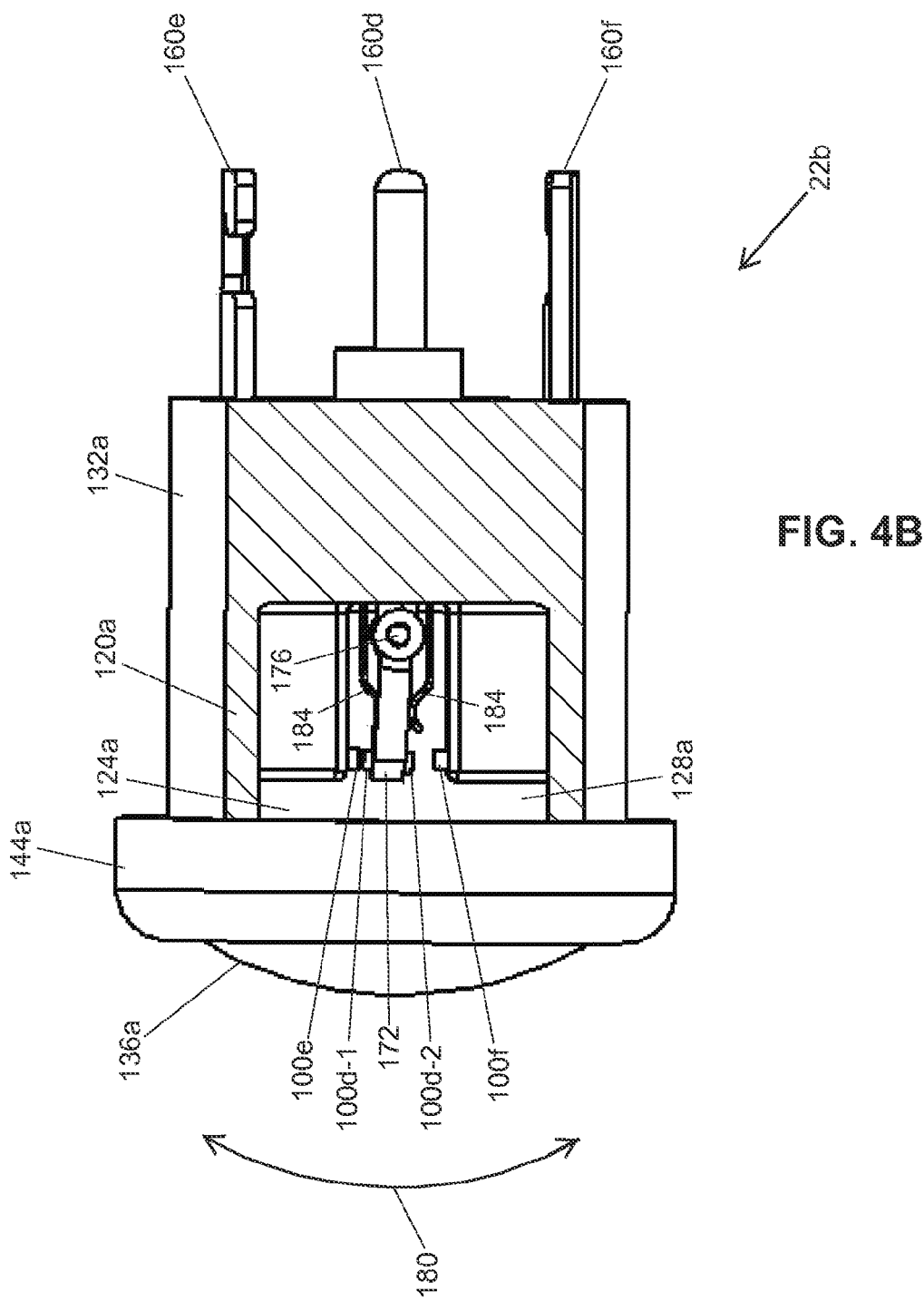
FIG. 4B depicts a cutaway side view of a second embodiment of a removable spark head usable with embodiments of the present handheld probes, such as the one of FIG. 4.

FIG. 4B depicts an enlarged cutaway side view of a second embodiment of a removable spark head or module 22*b*. In the embodiment shown, spark head or module 22*b* comprises a sidewall 120*a* defining a spark chamber 124*a*, and a plurality of electrodes 100*d*-1, 100*d*-2, 100, 100*f* disposed in the spark chamber. In the embodiment shown, spark chamber 124*a* is filled with liquid 128*a* which may be similar to liquid 128 and/or 54. At least a portion of sidewall 120*a* comprises an acoustically permeable or transmissive material (e.g., a polymer such as polyethylene) configured to permit sound waves and/or shockwaves generated at the electrodes to travel through sidewall 120*a* and through chamber 18*a* (FIG. 4). For example, in the embodiment shown, spark head 22*b* includes a cup-shaped member 132*a* that may be configured to be acoustically reflective and an acoustically permeable cap member 136*a*. In this embodiment, cap member 136*a* is dome shaped to approximate the curved shape of an expanding wavefront that originates at the electrodes and to compress the skin when applied with moderate pressure. Cap member 136*a* can be coupled to cup-shaped member 132*a* with an O-ring or gasket (not shown, but similar to 140) and a retaining collar 144*a*. In the embodiment shown, cup-shaped member 132*a* has a cylindrical shape with a circular cross-section (e.g., with a diameter of 2 inches or less). In some embodiments, cup-shaped member 132*a* can also include bayonet-style pins (not shown, but similar to 148, 152) configured to align with corresponding grooves in head 46*a* of probe 38*a* to lock the position of spark head 22*b* relative to the probe.

In the embodiment shown, conductors 160*d*, 160*e*, 160*f* extending through a rear portion (opposite outlet cap member 136*a*) of cup-shaped member 132*a*, as shown. In this embodiment, central conductor 160*d* and peripheral conductors 160*e*, 160*f* can be molded into sidewall 120*a* such that grommets and the like are not necessary to seal the interface between the sidewall and the conductors. In the embodiment shown, a central conductor 160*d* serves as a ground to corresponding center electrodes 100*d*-1 and 100*d*-2, which are also in electrical communication with each other. Peripheral conductors 160*e*, 160*f* are in communication with peripheral electrodes 100*e*, 100*f* to generate sparks across the spark gap between electrodes 100*d*-1 and 100*e*, and between electrodes 100*d*-2 and 100*f*. It should be understood that while two spark gaps are shown, any number of spark gaps may be used, and may be limited only by the spacing and size of the spark gaps. For example, other embodiments include 3, 4, 5, 6, 7, 8, 9, 10, or even more spark gaps.

In the embodiment shown, central electrodes 100*d*-1 and 100*d*-2 are carried by, and may be unitary with, an elongated member 172 extending into chamber 124*a* toward cap member 136*a* from sidewall 120*a*. In this embodiment, member 172 is mounted to a hinge 176 (which is fixed relative to sidewall 120*a*) to permit the distal end of the member (adjacent electrodes 100*d*-1, 100*d*-2 to pivot back and forth between electrodes 100*e* and 100*f*, as indicated by arrows 180. In the embodiment shown, the distal portion of member 172 is biased toward electrode 100*e* by spring arms 184. In this embodiment, spring arms 184 are configured to position electrode 100*d*-1 at an initial spark gap distance from electrode 100*e*. Upon application of an electrical potential (e.g., via a pulse-generation system, as described elsewhere in this disclosure) across electrodes 100*d*-1 and 100*e*, a spark will arc between these two electrodes to release an electric pulse to vaporize liquid between these two electrodes. The expansion of vapor between these two electrodes drives member 172 and electrode 100*d*-2 downward toward electrode 100*f*. During the period of time in which member 172 travels downward, the pulse-generation system can re-charge and apply an electric potential between electrodes 100*d*-2 and 100*f*, such that when the distance between electrodes 100*d*-2 and 100*f* becomes small enough, a spark will arc between these two electrodes to release the electric pulse to vaporize liquid between these two electrodes. The expansion of vapor between electrodes 100*d*-2 and 100*f* then drives member 172 and electrode 100*d*-1 upward toward electrode 100*e*. During the period of time in which member 172 travels upward, the pulse-generation system can re-charge and apply an electric potential between electrodes 100*d*-1 and 100*e*, such that when the distance between electrodes 100*d*-1 and 100*e* becomes small enough, a spark will arc between these two electrodes to release the electric pulse and vaporize liquid between these two electrodes, causing the cycle to begin again. In this way, member 172 oscillates between electrodes 100*e* and 100*f* until the electric potential ceases to be applied to the electrodes.

The exposure to high-rate and high-energy electric pulses, especially in liquid, subjects the electrodes to rapid oxidation, erosion, and/or other deterioration that can vary the spark gap distance between electrodes if the electrodes are held in fixed positions (e.g., requiring electrodes to be replaced and/or adjusted). However, in the embodiment of FIG. 2B, the pivoting of member 172 and electrodes 100*d*-1, 100*d*-2 between electrodes 100*e* and 100*f* effectively adjusts the spark gap for each spark. In particular, the distance between electrodes at which current arcs between the electrodes is a function of electrode material and electric potential. As such, once the nearest surfaces (even if eroded) of adjacent electrodes (e.g., 100*d*-1 and 100*e*) reach a spark gap distance for a given embodiment, a spark is generated between the electrodes. As such, member 172 is configured to self-adjust the respective spark gaps between electrodes 100*d*-1 and 100*e*, and between electrodes 100*d*-2 and 100*f*.

Another example of an advantage of the present movable electrodes, as in FIG. 4B, is that multiple coils are not required as long as the electrodes are positioned such that only one pair of electrodes is within arcing distance at any given time, and such a single coil or coil system is configured to recharge in less time than it takes for member 172 to pivot from one electrode to the next. For example, in the embodiment of FIG. 4B, an electric potential may simultaneously be applied to electrodes 100*e* and 100*f* with electrodes 100*d*-1 and 100*d*-2 serving as a common ground, with the electric potential such that a spark will only arc between electrodes 100*d*-1 and 100*e* when member 172 is pivoted upward relative to horizontal (in the orientation shown), and will only arc between electrodes 100*d*-2 and 100*f* when member 172 is pivoted downward relative to horizontal. As such, as member 172 pivots upward and downward as described above, a single coil or coil system can be connected to both of peripheral electrodes 100*e*, 100*f* and alternately discharged through each of the peripheral electrodes. In such embodiments, the pulse rate can be adjusted by selecting the physical properties of member 172 and spring arms 184. For example, the properties (e.g., mass, stiffness, cross-sectional shape and area, length, and/or the like) of member 172 and the properties (e.g., spring constant, shape, length, and/or the like) of spring arms 184 can be varied to adjust a resonant frequency of the system, and thereby the pulse rate of the spark head or module 22*b*. Similarly, the viscosity of liquid 128*a* may be selected or adjusted (e.g., increased to reduce the speed of travel of arm 184, or decreased to increase the speed of travel of arm 184).

Another example of an advantage of the present movable electrodes, as in FIG. 4B, is that properties (e.g., shape, cross-sectional area, depth, and the like) of the electrodes can be configured to achieve a known effective or useful life for the spark head (e.g., one 30-minute treatment) such that spark head 22*b* is inoperative or of limited effectiveness after that designated useful life. Such a feature can be useful to ensure that the spark head is disposed of after a single treatment, such as, for example, to ensure that a new, sterile spark head is used for each patient or area treated to minimize potential cross-contamination between patients or areas treated.

Figure 4C:
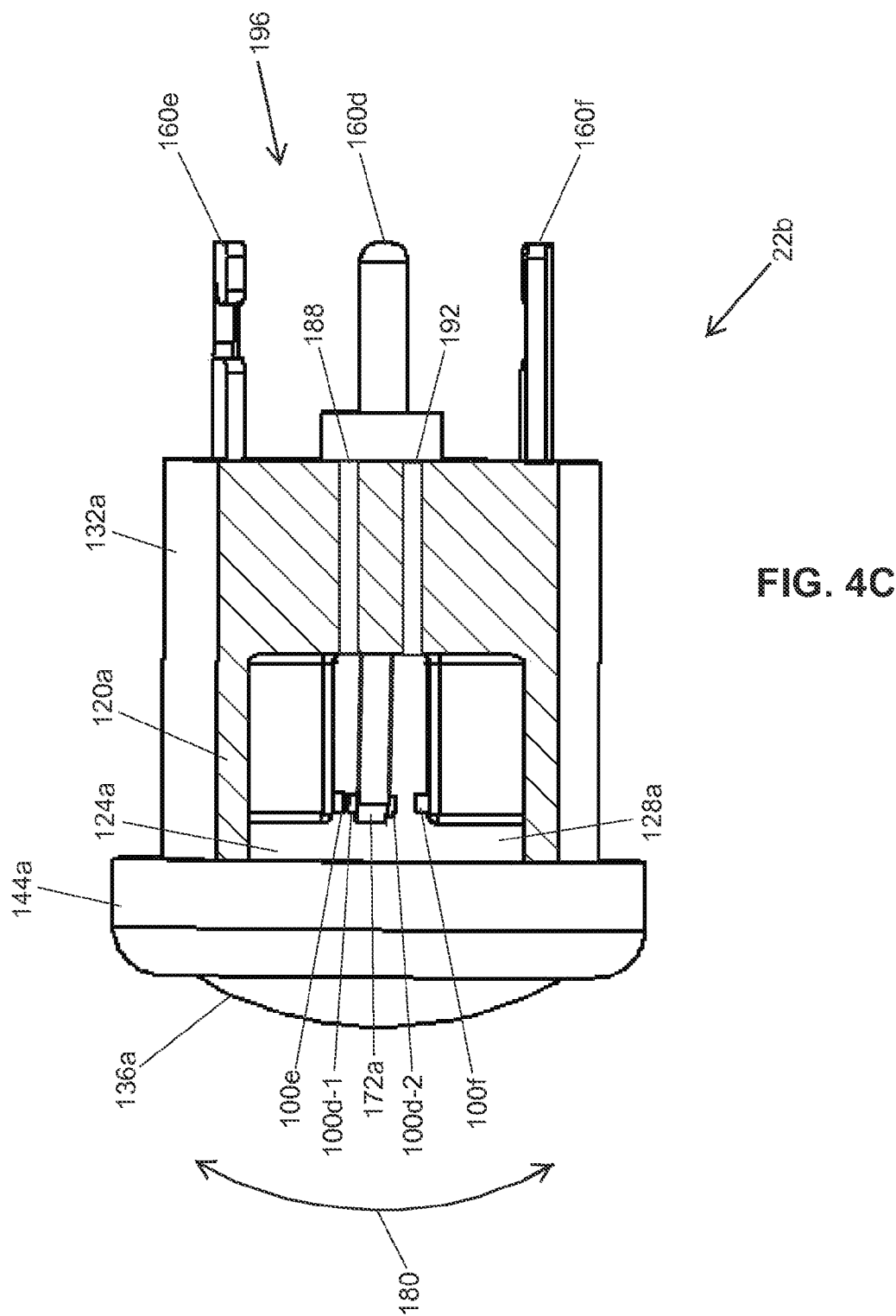
FIG. 4C depicts a cutaway side view of a third embodiment of a removable spark head usable with embodiments of the present handheld probes, such as the one of FIG. 4.

FIG. 4C depicts an enlarged cutaway side view of a third embodiment of a removable spark head or module 22*c*. Spark head 22*c* is substantially similar to spark head 22*b*, except as noted below, and similar reference numerals are therefore used to designate structures of spark head 22*c* that are similar to corresponding structures of spark head 22*b*. The primary difference relative to spark head 22*b* is that spark head 22*c* includes a beam 172*a* that does not have a hinge, such that flexing of the beam itself provides the movement of electrodes 100*d*-1 and 100*d*-2 in the up and down directions indicated by arrows 180, as described above for spark head 22*b*. In this embodiment, the resonant frequency of spark head 22*c* is especially dependent on the physical properties (e.g., mass, stiffness, cross-sectional shape and area, length, and/or the like) of beam 172*a*. As described for spring arms 184 of spark head 22*b*, beam 172*a* is configured to be biased toward electrode 100*e*, as shown, such that electrode 100*d*-1 is initially positioned at an initial spark gap distance from electrode 100*e*. The function of spark head 22*c* is similar to the function of spark head 22*b*, with the exception that beam 172*a* itself bends and provides some resistance to movement such that hinge 176 and spring arms 184 are unnecessary.

In the embodiment shown, spark head 22*b* also includes liquid connectors or ports 188, 192 via which liquid can be circulated through spark chamber 124*b*. In the embodiment shown, a proximal end 196 of spark head 22*b* serves as a combined connection with two lumens for liquid (connectors or ports 188, 192) and two or more (e.g., three, as shown) electrical conductors (connectors 160*d*, 160*e*, 160*f*). In such embodiments, the combined connection of proximal end 196 can be coupled (directly or via a probe or handpiece) to a combined tether or cable having two liquid lumens (corresponding to connectors or ports 188, 192), and two or more electrical conductors (e.g., a first electrical conductor for connecting to connector 160*d* and a second electrical conductor for connecting to both peripheral connectors 160*e*, 160*f*). Such a combined tether or cable can couple the spark head (e.g., and a probe or handpiece to which the spark head is coupled) to a pulse-generation system having a liquid reservoir and pump such that the pump can circulate liquid between the reservoir and the spark chamber. In some embodiments, cap member 136*a* is omitted such that connectors or ports 188, 192 can permit liquid to be circulated through a larger chamber (e.g., 18*a*) of a handpiece to which the spark head is coupled. Likewise, a probe or handpiece to which spark head 22*a* is configured to be coupled can include electrical and liquid connectors corresponding to the respective electrical connectors (160*d*, 160*e*, 160*f*) and ports (188, 192) of the spark head such that the electrical and liquid connectors of the spark head are simultaneously connected to the respective electrical and liquid connectors of the probe or handpiece as the spark module is coupled to the handpiece (e.g., via pressing the spark head and probe together and/or a twisting or rotating the spark head relative probe).

In the present embodiments, a pulse rate of a few Hz to many KHz (e.g., up to 5 MHz) may be employed. Because the fatiguing event produced by a plurality of pulses, or shockwaves, is generally cumulative at higher pulse rates, treatment time may be significantly reduced by using many moderately-powered shockwaves in rapid succession rather than a few higher powered shockwaves spaced by long durations of rest. As noted above, at least some of the present embodiments (e.g., those with multiple spark gaps) enable electro-hydraulic generation of shockwaves at higher rates. For example, FIG. 5A depicts a timing diagram 200 enlarged to show two sequences of voltage pulses 204, 208 applied to the electrodes of the present embodiments with a delay period 212 in between, and FIG. 5B depicts a timing diagram 216 showing a greater number of voltage pulses applied to the electrodes of the present embodiments.

In additional embodiments that are similar to any of spark head 22*a*, 22*b*, 22*c*, a portion of the respective sidewall (120, 120*a*, 120*b*) may be omitted such that the respective spark chamber (124, 124*a*, 124*b*) is also omitted or left open such that liquid in a larger chamber (e.g., 18 or 18*a*) of a corresponding handpiece can freely circulate between the electrodes. In such embodiments, the spark chamber (e.g., sidewall 120, 120*a*, 120*b* can include liquid connectors or liquid may circulate through liquid ports that are independent of spark chamber (e.g., as depicted in FIG. 4).

A series of events (sparks) initiated by a plurality of bursts or groups 204 and 208 delivered with the present systems and apparatuses can comprise a higher pulse rate (PR) that can reduce treatment time relative to lower PRs which may need to be applied over many minutes. The embodiments can be used to deliver shockwaves at the desired pulse rate.

Figure 6:
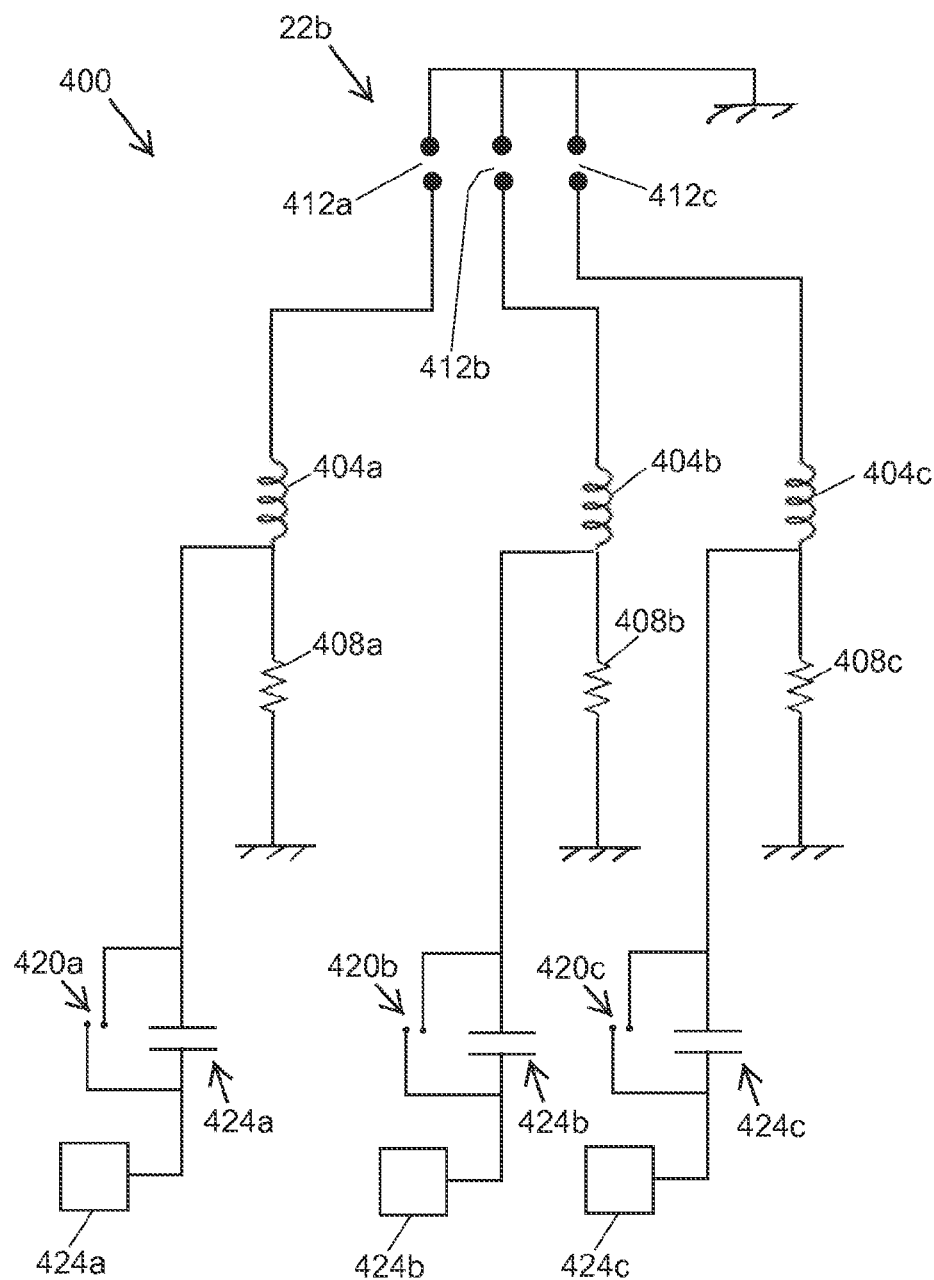
FIG. 6 depicts a schematic diagram of one embodiment of a multi-gap pulse-generation system for use in or with some embodiments of the present systems.

FIG. 6 depicts a schematic diagram of one embodiment 400 of a pulse-generation system for use in or with some embodiments of the present systems. In the embodiment shown, circuit 400 comprises a plurality of charge storage/discharge circuits each with a magnetic storage or induction type coil 404*a*, 404*b*, 404*c* (e.g., similar to those used in automotive ignition systems). As illustrated, each of coils 404*a*, 404*b*, 404*c*, may be grounded via a resistor 408*a*, 408*b*, 408*c* to limit the current permitted to flow through each coil, similar to certain aspects of automotive ignition systems. Resistors 408*a*, 408*b*, 408*c* can each comprise dedicated resistors, or the length and properties of the coil itself may be selected to provide a desired level of resistance. The use of components of the type used automotive ignition systems may reduce costs and improve safety relative to custom components. In the embodiment shown, circuit 400 includes a spark head 22*b* that is similar to spark head 22*a* with the exceptions that spark head 22*b* includes three spark gaps 412*a*, 412*b*, 412*c* instead of two, and that each of the three spark gaps is defined by a separate pair of electrodes rather than a common electrode (e.g., 100*a*)

cooperating with multiple peripheral electrodes. It should be understood that the present circuits may be coupled to peripheral electrodes 100b, 100c of spark head 22a to generate sparks across the spark gaps defined with common electrode 22a, as shown in FIG. 4A. In the embodiment shown, each circuit is configured to function similarly. For example, coil 404a is configured to collect and store a current for a short duration such that, when the circuit is broken at switch 420a, the magnetic field of the coil collapses and generates a so-called electromotive force, or EMF, that results in a rapid discharge of capacitor 424a across spark gap 412a.

The RL or Resistor-Inductance time constant of coil 404a—which may be affected by factors such as the size and inductive reactance of the coil, the resistance of the coil windings, and other factors—generally corresponds to the time it takes to overcome the resistance of the wires of the coil and the time to build up the magnetic field of the coil, followed by a discharge which is controlled again by the time it takes for the magnetic field to collapse and the energy to be released through and overcome the resistance of the circuit. This RL time constant generally determines the maximum charge-discharge cycle rate of the coil. If the charge-discharge cycle is too fast, the available current in the coil may be too low and the resulting spark impulse weak. The use of multiple coils can overcome this limitation by firing multiple coils in rapid succession for each pulse group (e.g., 204, 208 as illustrated in FIG. 5A). For example, two coils can double the practical charge-discharge rate by doubling the (combined) current and resulting spark impulse, and three (as shown) can effectively triple the effective charge-discharge rate. When using multiple spark gaps, timing can be very important to proper generation of spark impulses and resulting liquid vaporization and shockwaves. As such, a controller (e.g., microcontroller, processer, FPGA, and/or the like) may be coupled to each of control points 428a, 428b, 428c to control the timing of the opening of switches 420a, 420b, 420c and resulting discharge of capacitors 424a, 424b, 424c and generation of shockwaves.

Figure 7:
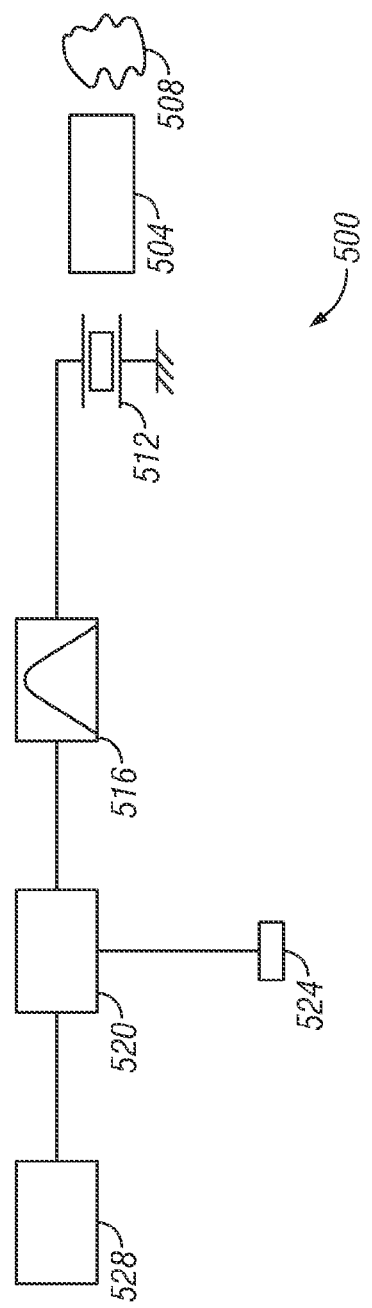
FIG. 7 depicts a block diagram of an embodiment of a radio-frequency (RF) powered acoustic ablation system.

FIG. 7 depicts a block diagram of an embodiment 500 of a radio-frequency (RF) powered acoustic shockwave generation system. In the embodiment shown, system 500 comprises a nonlinear medium 504 (e.g., as in acoustic-delay chamber 58 or nonlinear member described above) that provides an acoustic path to from a transducer 512 to target tissue 508 to produce practical harmonic or acoustic energy (e.g., shockwaves). In the embodiment shown, transducer 512 is powered and controlled through bandpass filter and tuner 516, RF power amplifier 520, and control switch 524. The system is configured such that actuation of switch 524 activates a pulse generator 528 to produce timed RF pulses that drive amplifier 520 in a predetermined fashion. A typical driving waveform, for example, may comprise a sine wave burst (e.g., multiple sine waves in rapid succession). For example, in some embodiments, a typical burst may have a burst length of 10 milliseconds and comprise sine waves having a period duration of 0.1 (frequency of 100 MHz) to 100 microseconds (frequency of 10 Hz).

Figure 8A:
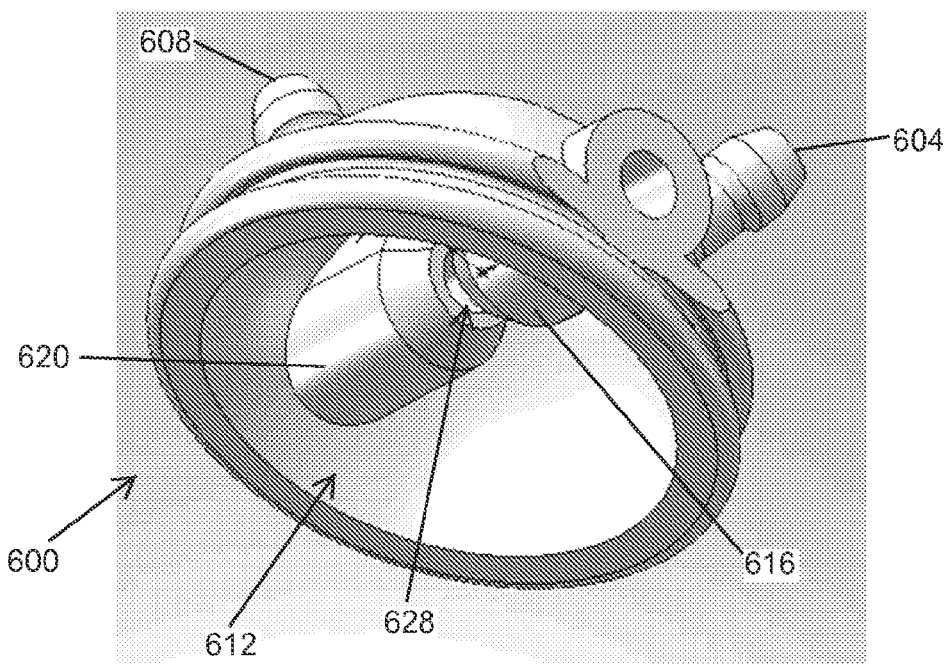
FIGS. 8A-8B depict perspective and cross-sectional views of a first embodiment of a spark chamber housing.
Figure 8B:
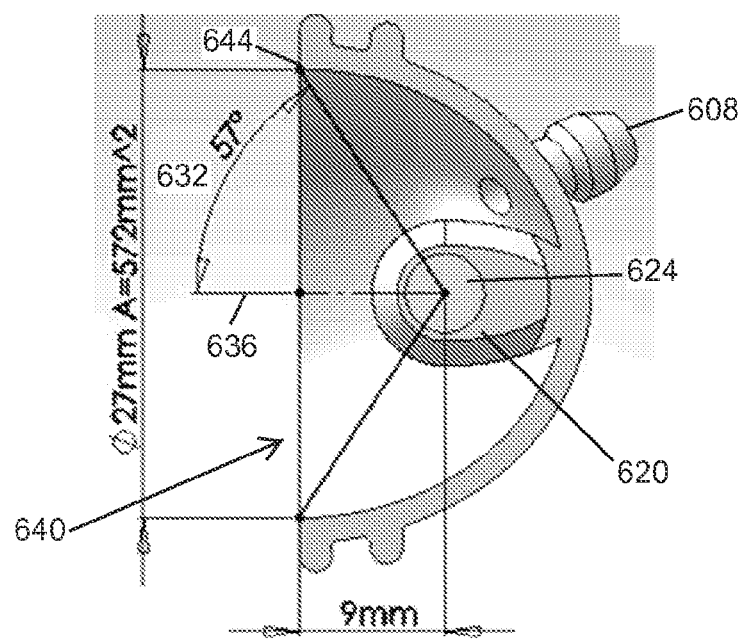
Figure 9:
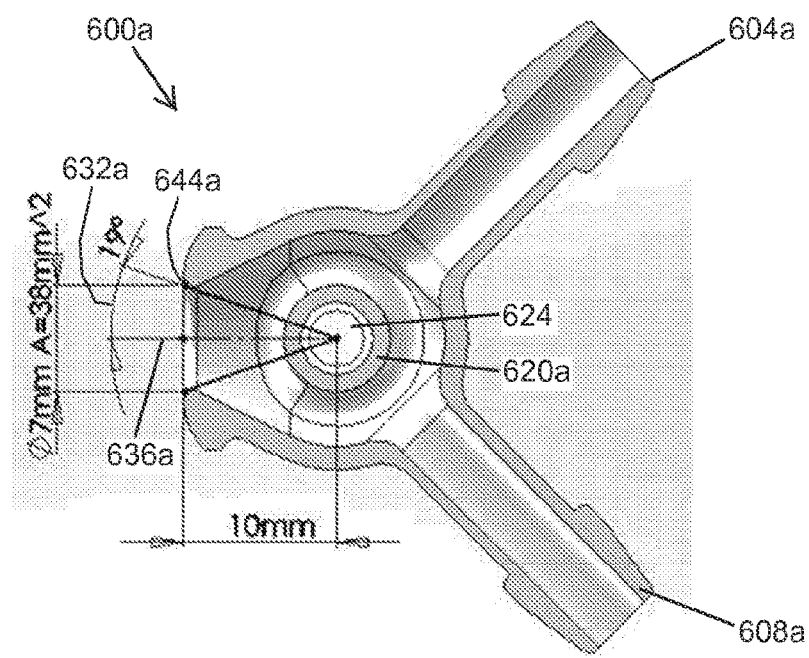
FIG. 9 depicts a cross-sectional view of a second embodiment of spark chamber housing.

FIGS. 8A-8B and 9 depict two different spark chamber housings. The embodiments of FIGS. 8A-8B depict one embodiment of a spark chamber housing. Housing 600 is similar in some respects to the portion of housing 14a that defines head 46a of probe 38a (FIG. 4). For example, housing 600 includes fittings 604, 608 to permit liquid to be circulated through spark chamber 612. In the embodiment shown, housing 600 includes electrode supports 616 and 620 through which electrodes 624 can be inserted to define a spark gap 628 (e.g., of 0.127 mm or 0.005 inches in the experiments described below). However, housing 600 has an elliptical inner surface shaped to reflect the shockwaves that initially travel backwards from the spark gap into the wall. Doing so has the advantage of producing, for each shockwave generated at the spark gap, a first or primary shockwave that propagates from the spark gap to outlet 640, followed by a secondary shockwave that propagates first to the elliptical inner wall and is then reflected back to outlet 640.

In this embodiment, supports 616 and 620 are not aligned with (rotated approximately 30 degrees around chamber 612 relative to) fittings 604, 608. In the embodiment shown, housing 600 has a hemispherical shape and electrodes 624 are positioned such that an angle 632 between a central axis 636 through the center of shockwave outlet 640 and a perimeter 644 of chamber 612 is about 57 degrees. Other embodiments can be configured to limit this angular sweep and thereby direct the sound waves and/or shockwaves through a smaller outlet. For example, FIG. 9 depicts a cross-sectional view of a second embodiment of a spark chamber housing. Housing 600a is similar to housing 600, with the exception that fittings 604a, 608a are rotated 90 degrees relative to support 620a. Housing 600a also differs in that chamber 612a includes a hemispherical rear or proximal portion and a frusto-conical forward or distal portion. In this embodiment, electrodes 624a are positioned such that an angle 632a between a central axis 636a through the center of shockwave outlet 640a and a perimeter 644a of chamber 612a is about 19 degrees.

Figure 10:
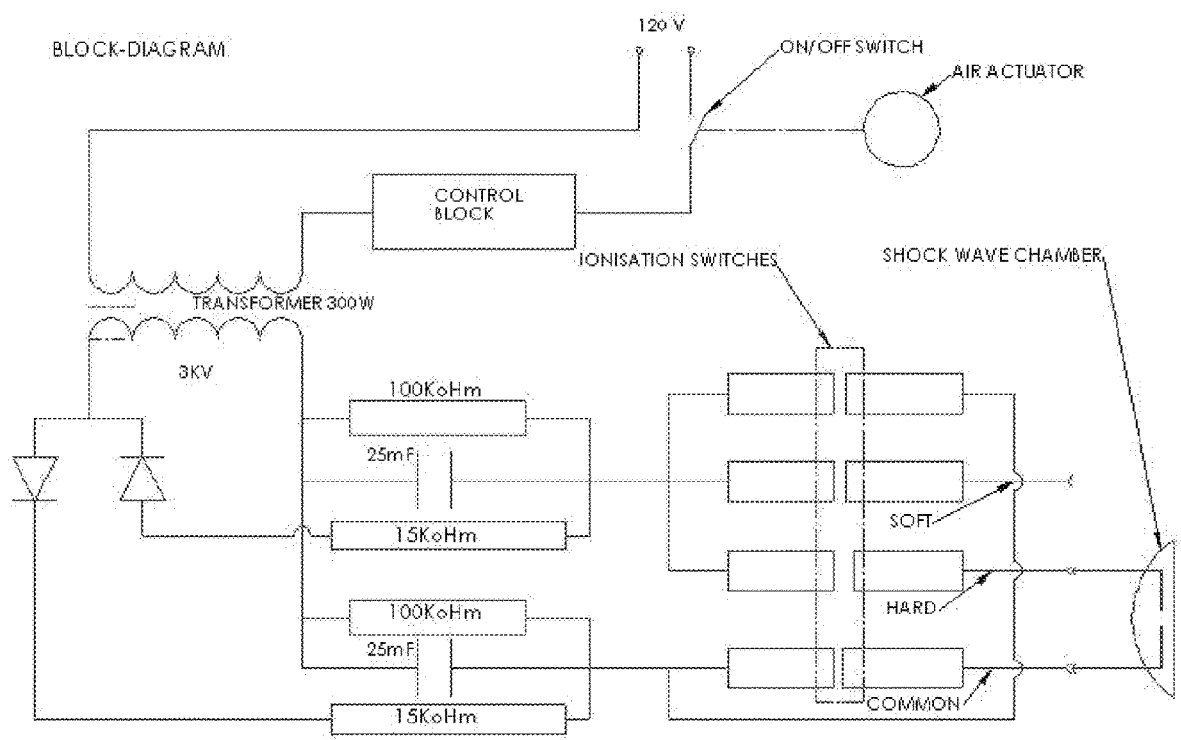
FIG. 10 depicts a schematic diagram of an electric circuit for a pulse-generation system.
Figure 11:
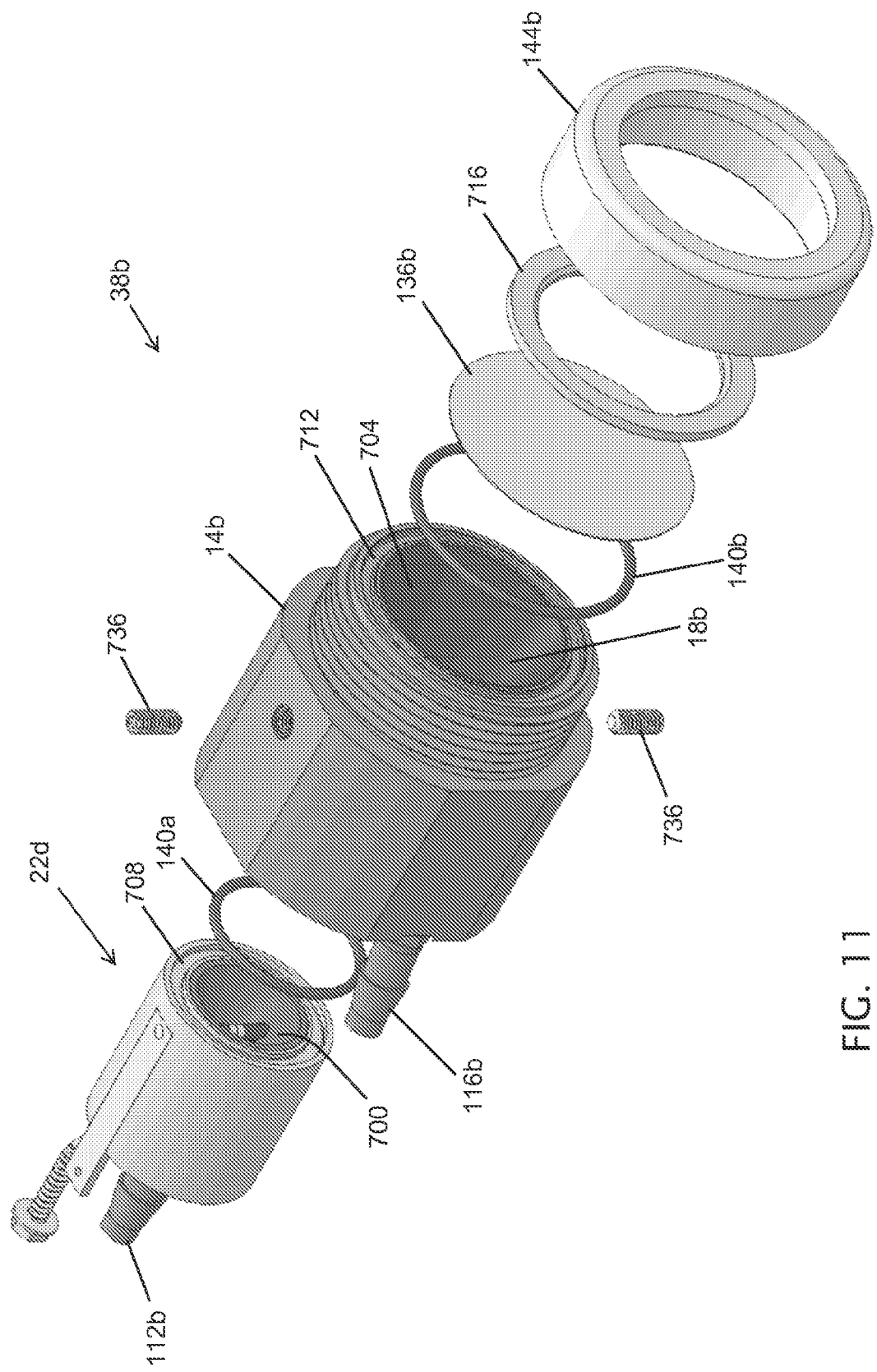
FIG. 11 depicts an exploded perspective view of a further embodiment of the present probes having a spark head or module.
Figure 13A:
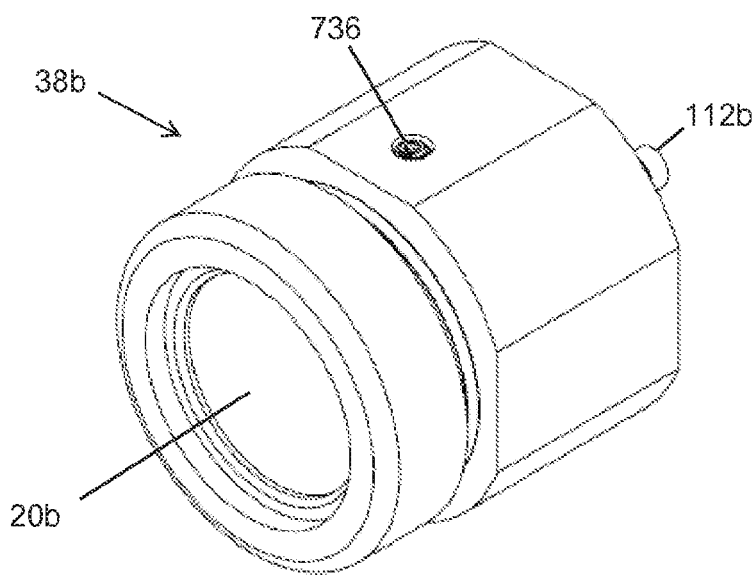
FIGS. 13A and 13B depict perspective and side cross-sectional views, respectively, of the probe of FIG. 11.
Figure 13B:
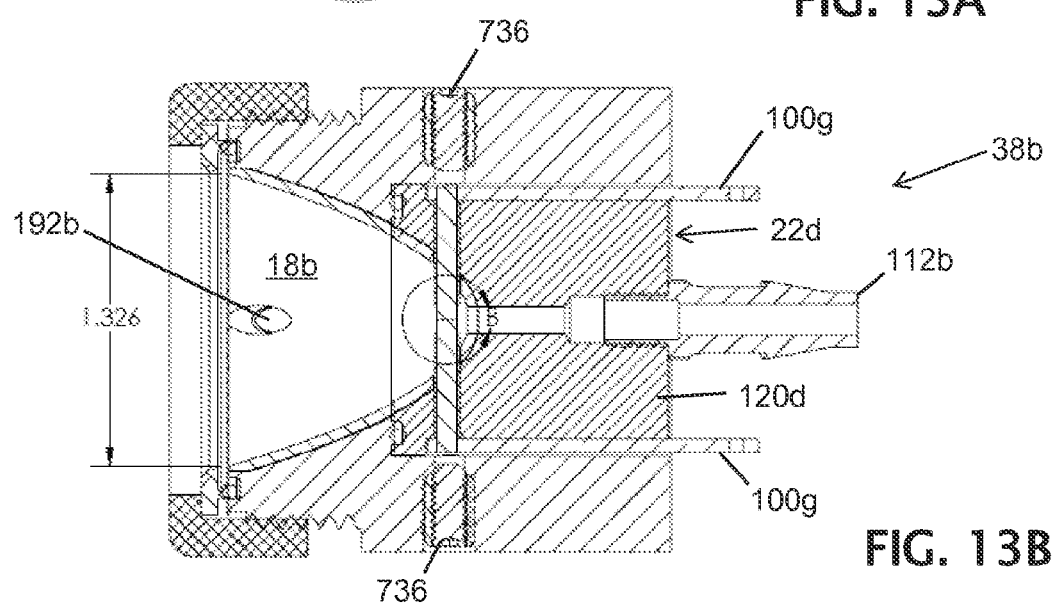
Figure 13C:
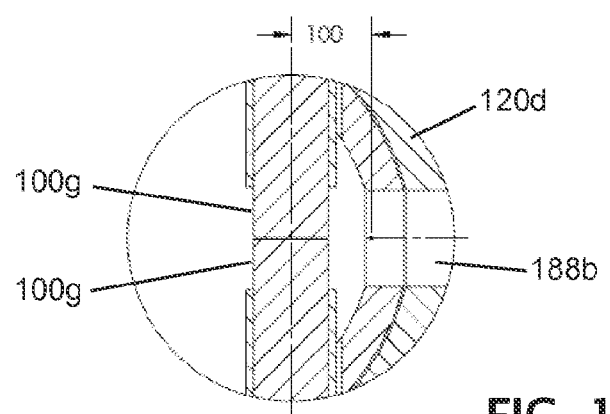
FIG. 13C depicts an enlarged side cross-sectional view of a spark gap of the probe of FIG. 11.

FIG. 10 depicts a schematic diagram of an electric circuit for a prototyped pulse-generation system used with the spark chamber housing of FIGS. 8A-8B. The schematic includes symbols known in the art, and is configured to achieve pulse-generation functionality similar to that described above. The depicted circuit is capable of operating in the relaxation discharge mode with embodiments of the present shockwave heads (e.g., 46, 46a, etc.). As shown, the circuit comprises a 110V alternating current (AC) power source, an on-off switch, a timer ("control block"), a step-up transformer that has a 3 kV or 3000V secondary voltage. The secondary AC voltage is rectified by a pair of high voltage rectifiers in full wave configuration. These rectifiers charge a pair of oppositely polarized 25 mF capacitors that are each protected by a pair of resistors (100 kΩ and 25 kΩ) in parallel, all of which together temporarily store the high-voltage energy. When the impedance of the shockwave chamber is low and the voltage charge is high, a discharge begins, aided by ionization switches, which are large spark gaps that conduct when the threshold voltage is achieved. A positive and a negative voltage flow to each of the electrodes so the potential between the electrodes can be up to about 6 kV or 6000 V. The resulting spark between the electrodes results in vaporization of a portion of the liquid into a rapidly-expanding gas bubble, which generates a shockwave. During the spark, the capacitors discharge and become ready for recharge by the transformer and rectifiers. In the experiments described below, the discharge was about 30 Hz, regulated only by the natural rate of charge and discharge—hence the term "relaxation oscillation." In other embodiments, the discharge rate can be higher (e.g., as high as 100 Hz), such as for the multi-gap configuration of FIG. 6.

A further embodiment 38b of the present (e.g., handheld) probes for use with some method embodiments are depicted in FIGS. 11-13C. Probe 38b is similar in some respects to probes 38 and 38a, and the differences are therefore primarily described here. In this embodiment, probe 38b comprises: a housing 14b defining a chamber 18b and a shockwave outlet 20b; a liquid disposed in chamber 18b; a plurality of electrodes (e.g., in spark head or module 22d) configured to be disposed in the chamber to define one or more spark gaps; and is configured to be coupled to a pulse-generation system (e.g., system 26 of FIG. 2) configured to apply voltage pulses to the electrodes at a rate of 10 Hz to 1000 Hz or at a rate of 10 Hz to 100 Hz.

In the embodiment shown, spark head 22d includes a housing 120d and a plurality of electrodes 100g that define a spark gap. In this embodiment, probe 38b is configured to permit liquid to be circulated through chamber 18b via liquid connectors or ports 112b and 116b, one of which is coupled to spark head 22d and the other of which is coupled to housing 14b, as shown. In this embodiment, housing 14b is configured to receive spark head 22d, as shown, such that housing 14b and housing 120d cooperate to define chamber 18b (e.g., such that spark head 22d and housing 14b include a complementary parabolic surfaces that cooperate to define the chamber). In this embodiment, housing 14b and spark head 22d includes acoustically-reflective liners 700, 704 that cover their respective surfaces that cooperate to define chamber 18b. In this embodiment, housing 120d of spark head 22d includes a channel 188b (e.g., along a central longitudinal axis of spark head 22d) extending between liquid connector 112b and chamber 18b and aligned with the spark gap between electrodes 100g such that circulating water will flow in close proximity and/or through the spark gap. In the embodiment shown, housing 14b includes a channel 192b extending between connection 116b and chamber 18b. In this embodiment, housing 120d includes a groove 708 configured to receive a resilient gasket or O-ring 140a to seal the interface between spark head 22d and housing 14b, and housing 14b includes a groove 712 configured to receive a resilient gasket or O-ring 140b to seal the interface between housing 14b and cap member 136b when cap member 136b is secured to housing 14b by ring 716 and retaining collar 144b.

In the embodiment shown, electrodes 100g each includes a flat bar portion 724 and a perpendicular cylindrical portion 728 (e.g., comprising tungsten for durability) in electrical communication (e.g., unitary with) bar portion 724 such that cylindrical portion 728 can extend through a corresponding opening 732 in spark head 22d into chamber 18b, as shown. In some embodiments, part of the sides of cylindrical portion 728 can be covered with an electrically insulative and/or resilient material (e.g., shrink wrap) such as, for example, to seal the interface between portion 728 and sidewall 120b. In this embodiment, sidewall 120b also includes longitudinal grooves 733 configured to receive bar portions 724 of electrodes 100g. In the embodiment shown, housing 14b also includes set screws 736 positioned to align with cylindrical portions 728 of electrodes 100g when spark head 22d is disposed in housing 14b, such that set screws 736 can be tightened to press cylindrical portions 728 inward to adjust the spark gap between the cylindrical portions of electrodes 100g. In some embodiments, spark head 22d is permanently adhered to housing 14b; however, in other embodiments, spark head 22d may be removable from housing 14b such as, for example, to permit replacement of electrodes 100g individually or as part of a new or replacement spark head 22d.

Figure 14:
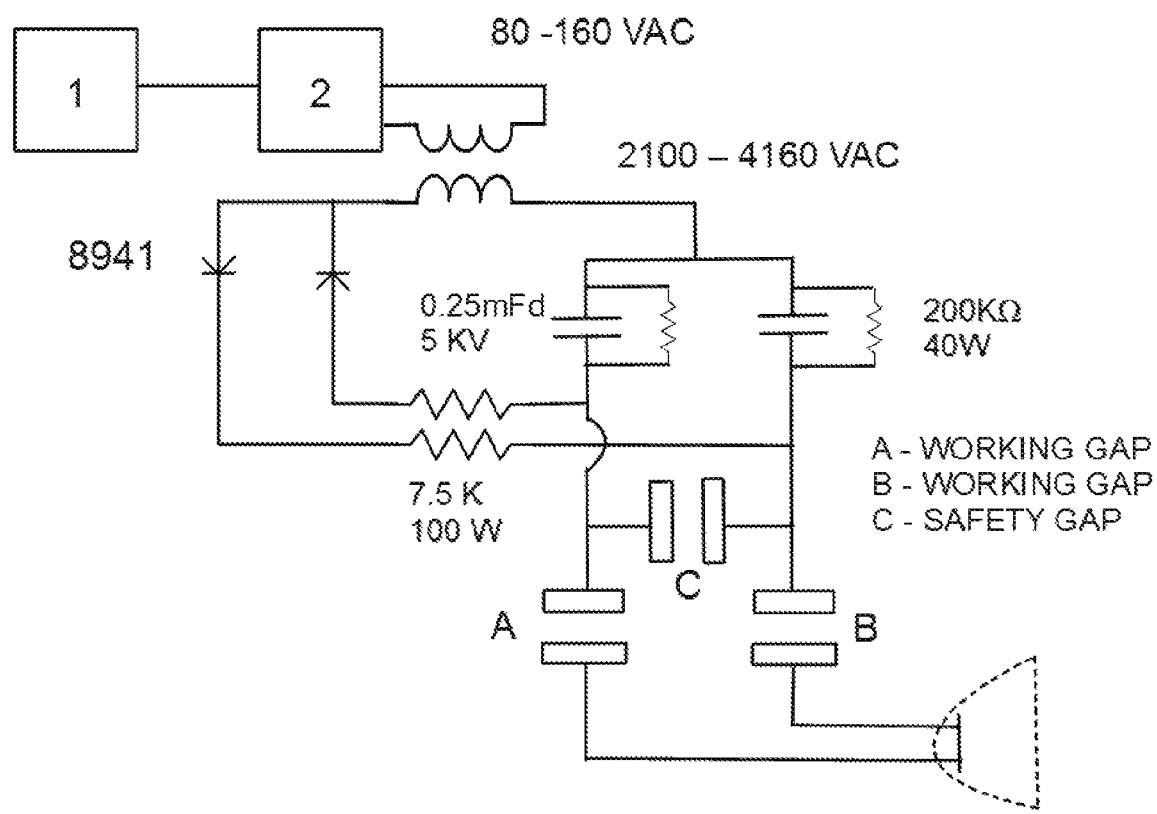
FIG. 14 depicts a schematic diagram of a second embodiment of an electric circuit for a prototyped pulse-generation system.

FIG. 14 depicts a schematic diagram of another embodiment of an electric circuit for a pulse-generation system. The circuit of FIG. 14 is substantially similar to the circuit of FIG. 10 with the primary exception that the circuit of FIG. 14 includes an arrangement of triggered spark gaps instead of ionization switches, and includes certain components with different properties than corresponding components in the circuit of FIG. 10 (e.g., 200 kΩ resistors instead of 100 kΩ resistors). In the circuit of FIG. 14, block "1" corresponds to a primary controller (e.g., processor) and block "2" corresponds to a voltage timer controller (e.g., oscillator), both of which may be combined in a single unit in some embodiments.

Experimental Results

Experiments were conducted on minipigs to observe effects of EH-generated shockwaves on adipose tissue.

EXAMPLE 1

Adipose Tissue Inflammation

A study was undertaken to evaluate the induction of inflammation in subcutaneous fat using high-frequency shockwave. A Gottingen minipig (~30 Kg) was anesthetized. The mid-ventral sites were prepared by removing the skin hair here using hair clippers and then razor. High-frequency shockwaves were then applied to the two treatment sites. Following the high frequency shockwave treatment, and 48 hours post treatment, biopsies were taken of treatment sites using 3 mm circular punch biopsy instruments. Tissue samples were placed in buffered formalin for microscopic examination.

The high frequency shockwave treatment protocols are shown in Table 1. The probe had a 30 mm diameter shockwave outlet window and was configured to generate electrohydraulic shockwaves. All five sites that were treated using different high frequency shockwave settings demonstrated inflammation in the subcutaneous fat. No evidence of cavitation or thermal damage was noted on any of the tissue in the slides.

| Site | Total J | J/P | Hz |
| --- | --- | --- | --- |
| 4.6 | 20,700 | 9.2 | 25 |
| 4.7 | 41,400 | 9.2 | 25 |
| 4.8 | 20,700 | 6.9 | 33 |
| 4.9 | 41,400 | 6.9 | 33 |
| 4.10 | 20,700 | 4.6 | 50 |

By way of example, histological evaluations of site 4.6 were conducted on the day of treatment and 2 days post treatment. As noted in Table 1, Site 4.6 was treated using a high frequency shockwave treatment for 90 seconds at 9.2 J/p at a rate of 25 Hz. The adipose tissue demonstrated marked inflammatory cell infiltration two days post treatment indicating that inflammation had been induced. Furthermore, there was no evidence of cavitation, thermal damage or other tissue damage at the treatment site.

EXAMPLE 2

Adipose Tissue Volume Loss

A study was undertaken to evaluate subcutaneous volume loss following treatment with high frequency shockwaves. A Gottingen minipig (~30 Kg) was prepared as described in Example 1. Two separate test sites (1.7, 1.8) were treated using high-frequency shockwaves (9.2j/p, 25 Hz, 240 seconds). The probe had a 30 mm diameter shockwave outlet window and was configured to generate electrohydraulic shockwaves.

Two weeks following the high frequency shockwave treatment, the amount of post-treatment volume change was assessed utilizing a Canfield Scientific Vectra three-dimensional camera and software. Volumetric pictures of the test sites (1.7, 1.8) were compared to adjacent control sites (Sites 1.9, 1.10). A loss of volume was indicated from the treated sites (1.7, 1.8). Furthermore, the skin for both test sites demonstrated discoloration of the overlying skin. This is consistent with the appearance skin overlying panniculitis. Thus, the discoloration likely indicates underlying inflammation.

EXAMPLE 3

Lipid Crystallization

A study was performed to demonstrate that non-cavitating, non-thermal, high intensity shockwaves when applied to adipose tissue results in the crystallization of the adipocyte lipids. A Gottingen Minipig (~30 Kg) was prepared as described in Example 1. Site 1.8 after treatment described in Example 2 was measured immediately following the high frequency shockwave treatment. A biopsy was taken of the subcutaneous fat at the treated site. For comparison, a biopsy was taken at a non-treated site. Samples of the biopsied tissues were stored in saline and then prepared for cross-polarized light microscopic examination to see if evidence of crystal nucleation had occurred. To aid in visualizing crystal nucleation, tissue samples were cooled to allow crystal growth at the crystal nucleation sites.

Both samples were heated to 45C, and then cooled to 0C for 45 minutes. The treated adipose sample had a luminosity of 34 compared to the control adipose sample's luminosity of 32. The bigger the luminosity value the brighter the sample which is indicative of more polarized crystals. Based on this study, the adipose tissue from high frequency shockwave treated sites had evidence of significant crystallization when compared to untreated adipose tissue.

The above specification and examples provide a description of the process and use of exemplary embodiments. Although certain embodiments have been described above with a certain degree of particularity, or with reference to one or more individual embodiments, those skilled in the art could make numerous alterations to the disclosed embodiments without departing from the scope of this invention. As such, the various illustrative embodiments of the present methods are not intended to be limited to the particular steps disclosed. Rather, they include all modifications and alternatives falling within the scope of the claims, and embodiments other than the one shown may include some or all of the features of the depicted embodiment. Further, where appropriate, aspects of any of the examples described above may be combined with aspects of any of the other examples described to form further examples having comparable or different properties and addressing the same or different problems. Similarly, it will be understood that the benefits and advantages described above may relate to one embodiment or may relate to several embodiments.

The claims are not intended to include, and should not be interpreted to include, means-plus- or step-plus-function limitations, unless such a limitation is explicitly recited in a given claim using the phrase(s) "means for" or "step for," respectively.

REFERENCES

[1] Manstein, D; Laubach, H; Watanabe, K; Farinelli, W et al. (2008). "Selective cryolysis: A novel method of non-invasive fat removal". Lasers in Surgery and Medicine 40 (9): 595-604.

[2] Krueger N, Mai S V, Luebberding S, Sadick N S, Cryolipolysis for noninvasive body contouring: clinical efficacy and patient satisfaction. Clinical, Cosmetic and Investigational Dermatology, 2014:7

[3] Ferraro G A, De Francesco F, Cataldo C, Rossano F, Nicoletti G, D'Andrea F, Synergistic effects of cryolipolysis and shock waves for noninvasive body contouring. Aesthetic Plast Surg. 2012 June; 36(3):666-7

The invention claimed is:

1. A method of treating a patient to reduce subcutaneous fat in a treatment area, where fat comprises fat cells having intracellular fat and interstitial space between the fat cells, the method comprising:
   directing a pressure wave generating probe to a treatment area of the patient; and
   emitting a plurality of pressure waves to the treatment area at a pulse rate of between 15 Hz and 1000 Hz,
   where the pressure wave generating probe comprises a pressure wave outlet window,
   where the pressure wave generating probe is configured to emit the plurality of pressure waves each having an energy density of between 0.5 mJ per $mm^2$ and 7.0 mJ per $mm^2$ at the pressure wave outlet window, and
   where the plurality of pressure waves are not focused prior to entering into the treatment area of the patient.

2. The method of claim 1, further comprising applying the plurality of pressure waves to an adipose tissue in the treatment area at:
   a pulse rate of between 25 and 500 HZ; and
   an energy density of between 2 and 7.0 mJ per $mm^2$ per pressure wave.

3. The method of claim 1, further comprising directing at least a portion of the plurality of pressure waves to the treatment area such that delivery of the at least a portion of the plurality of pressure waves to the treatment area reduces the appearance of cellulite in the treatment area.

4. The method of claim 1, where the plurality of pressure waves do not induce transient cavitation in an aqueous solution of the pressure wave generating probe.

5. The method of claim 2, where the plurality of pressure waves emitted by the pressure wave generating probe induce no adipose cell damage when treating the treatment area.

6. The method of claim 2, where the plurality of pressure waves emitted by the pressure wave generating probe increase a luminosity value of the adipose tissue associated with the treatment area.

7. The method of claim 1, where the plurality of pressure waves emitted by the pressure wave generating probe cause a volume loss of the treatment area.

8. The method of claim 1, where:
   the plurality of pressure waves include a pressure wave energy of between 2.0 and 7.0 mJ per $mm^2$ at the pressure wave outlet window; and
   the pressure wave outlet window has an area of between 0.5 and 20 $mm^2$.

9. A method of inducing inflammation of subcutaneous adipose tissue in a treatment area of a patient, the method comprising:
   directing a pressure wave generating probe to an external treatment area of the patient; and emitting a plurality of pressure waves to the treatment area at a pulse rate of between 15 Hz and 1000 Hz,
where the pressure wave generating probe comprises a pressure wave outlet window, and
where the pressure wave generating probe is configured to emit the plurality of pressure waves having between 0.5 and 7.0 mJ per $mm^2$ at the pressure wave outlet window.

10. The method of claim 9, where the plurality of pressure waves do not induce transient cavitation in an aqueous solution of the pressure wave generating probe.

11. The method of claim 9, where the treatment area is within a depth of 6 cm from a surface of the treatment area, and where the treatment area is a butt, thigh, stomach, waist, upper arm area, or a portion thereof.

12. The method of claim 9, where the plurality of pressure waves emitted from the pressure wave generating probe comprise substantially planar pressure waves.

13. The method of claim 9, where the plurality of pressure waves are continuously directed to the treatment area at the pulse rate for a time period between 90 seconds and 30 minutes.

14. The method of claim 13, further comprising, directing at least a portion of the plurality of pressure waves to the treatment area such that delivery of the at least a portion of the plurality of pressure waves to the treatment area:
increases one or more cytokines in blood serum of the patient;
increases an amount of lipid crystals within an adipose tissue within the treatment area;
induces inflammation in subcutaneous adipose tissue in the treatment area; or
combination thereof.

15. The method of claim 14, where the one or more cytokines comprises one or more of leptin, IL-6, or TNF-α.

16. The method of claim 9, where the plurality of pressure waves are emitted at a pulse rate of between 25 and 100 Hz.

17. An apparatus for treating a patient to reduce subcutaneous fat in a treatment area, where fat comprises fat cells having intracellular fat and interstitial space between the fat cells, the apparatus comprising:
a pressure wave generating probe configured to deliver a series of pressure waves to an external area of the patient, the pressure wave generating probe comprising:
a housing defining a chamber and a shockwave outlet, the chamber configured to be filled with a liquid; and
a plurality of electrodes disposed in the chamber to define one or more spark gaps;
where the pressure wave generating probe is configured to emit the series of pressure waves at an energy density of between 2.0 and 7.0 mJ per $mm^2$ at the shockwave outlet and induce no transient cavitation bubbles in a water-based medium, and
where, when the plurality of electrodes is coupled to a pulse generation system and when the chamber is filled with the liquid:
the plurality of electrodes is configured to receive voltage pulses from the pulse generation system at a rate of between 10 Hz and 5 MHz such that portions of the liquid are vaporized to generate the series of pressure waves that propagate through the liquid and the shockwave outlet.

18. The apparatus of claim 17, where the series of pressure waves comprise therapeutic shockwaves, and where the pressure wave generating probe is configured to generate a pressure wave having a power between 2.0 mJ per $mm^2$ to 5 mJ per $mm^2$.

19. The apparatus of claim 17, where the pressure wave generating probe is configured to emit, at the shockwave outlet a shockwave comprising a shockwave front of less than 20 ns in an aqueous solution, and where a pressure wave outlet window associated with the shockwave outlet has an area of 0.5 $cm^2$ to 20 $cm^2$.

20. The apparatus of claim 17, where the pressure wave generating probe is configured to emit the series of pressure waves at a pulse rate of between 25 Hz and 1000 Hz.

21. The apparatus of claim 17, where the pressure wave generating probe further comprises:
an electrohydraulic wave generator; and
a probe handle configured to be removeably coupled to the pressure wave generating probe such that the housing and plurality of electrodes are removable from the probe handle as a single unit; and
where the housing comprises a parabolic surface that defines the chamber.

22. The apparatus of claim 21, where the housing includes one or more liquid ports in fluid communication with the chamber and configured to allow the liquid to circulate between the chamber and the probe handle when the pressure wave generating probe is coupled to the probe handle.

23. The apparatus of claim 21, where:
the pressure wave generating probe includes a first electrical connector configured to couple the plurality of electrodes to the pulse generation system; and
the housing, the plurality of electrodes, and the first electrical connector are removable from the probe handle as a single unit.

24. The apparatus of claim 21, where the pressure wave generating probe further includes a hinge coupled to a first electrode of the plurality of electrodes, the hinge configured to enable a change in a physical position of the first electrode with respect to a second electrode of the plurality of electrodes.

25. The apparatus of claim 21, where a position of a first electrode of the plurality of electrodes with respect to a second electrode of the plurality of electrodes is movable from a first position within the chamber to a second position within the chamber.

* * * * *

UNITED STATES PATENT AND TRADEMARK OFFICE
CERTIFICATE OF CORRECTION

| | |
|---|---|
| PATENT NO. | : 11,229,575 B2 |
| APPLICATION NO. | : 15/573353 |
| DATED | : January 25, 2022 |
| INVENTOR(S) | : Christopher C. Capelli and David Robertson |

It is certified that error appears in the above-identified patent and that said Letters Patent is hereby corrected as shown below:

On the Title Page

In Item (86), delete "PCT/US2016/320069" and insert --PCT/US2016/032069-- therefor.

In Item (57) Abstract, Line 7, delete "100Hz" and insert --1000Hz-- therefor.

Signed and Sealed this
Tenth Day of May, 2022

Katherine Kelly Vidal
*Director of the United States Patent and Trademark Office*